(12) United States Patent
Streisand et al.

(10) Patent No.: US 8,642,034 B2
(45) Date of Patent: Feb. 4, 2014

(54) USE OF TGF-β ANTAGONISTS TO TREAT INFANTS AT RISK OF DEVELOPING BRONCHOPULMONARY DYSPLASIA

(75) Inventors: James B. Streisand, Sudbury, MA (US); Jesse D. Roberts, Jr., Brighton, MA (US)

(73) Assignee: Genzyme Corporation, Cambridge, MA (US)

( * ) Notice: Subject to any disclaimer, the term of this patent is extended or adjusted under 35 U.S.C. 154(b) by 520 days.

(21) Appl. No.: 12/444,059

(22) PCT Filed: Oct. 3, 2007

(86) PCT No.: PCT/US2007/021234
§ 371 (c)(1),
(2), (4) Date: Jun. 9, 2009

(87) PCT Pub. No.: WO2008/060371
PCT Pub. Date: May 22, 2008

(65) Prior Publication Data
US 2010/0008911 A1    Jan. 14, 2010

Related U.S. Application Data

(60) Provisional application No. 60/827,933, filed on Oct. 3, 2006.

(51) Int. Cl.
*A61K 39/395* (2006.01)
*A61K 38/17* (2006.01)
*C07K 16/22* (2006.01)
*C07K 16/28* (2006.01)
*C07K 14/495* (2006.01)
*C07K 14/71* (2006.01)
*C07K 14/785* (2006.01)

(52) U.S. Cl.
USPC .................. 424/133.1; 424/143.1; 424/145.1; 424/158.1; 514/1.5; 514/15.5; 530/350; 530/387.3; 530/388.22; 530/388.23

(58) Field of Classification Search
None
See application file for complete search history.

(56) References Cited

U.S. PATENT DOCUMENTS

| 5,520,926 | A | 5/1996 | Ferguson |
|---|---|---|---|
| 5,571,714 | A | 11/1996 | Dasch et al. |
| 5,583,103 | A | 12/1996 | Ruoslahti et al. |
| 5,654,270 | A | 8/1997 | Ruoslahti et al. |
| 5,683,988 | A | 11/1997 | Chung |
| 5,693,607 | A | 12/1997 | Segarini et al. |
| 5,693,610 | A | 12/1997 | Matsunaga et al. |
| 5,705,609 | A | 1/1998 | Ruoslahti et al. |
| 5,726,149 | A | 3/1998 | Ruoslahti et al. |
| 5,772,995 | A | 6/1998 | Fakhrai et al. |
| 5,772,998 | A | 6/1998 | Dasch et al. |
| 5,783,185 | A | 7/1998 | Dasch et al. |
| 5,821,227 | A | 10/1998 | Dennis et al. |
| 5,821,234 | A | 10/1998 | Dzau |
| 5,824,655 | A | 10/1998 | Border |
| 5,830,847 | A | 11/1998 | Letarte et al. |
| 5,869,462 | A | 2/1999 | Dzau |
| 6,001,969 | A | 12/1999 | Lin et al. |
| 6,008,011 | A | 12/1999 | Lin et al. |
| 6,010,872 | A | 1/2000 | Lin et al. |
| 6,015,693 | A | 1/2000 | Letarte et al. |
| 6,184,226 | B1 | 2/2001 | Chakravarty et al. |
| 7,527,791 | B2* | 5/2009 | Adams et al. ............... 424/145.1 |
| 2002/0076799 | A1* | 6/2002 | Wang ............................ 435/226 |
| 2003/0180301 | A1 | 9/2003 | Keshavjec et al. |
| 2004/0029176 | A1 | 2/2004 | Yoon |
| 2004/0053838 | A1 | 3/2004 | Smith et al. |
| 2004/0266025 | A1 | 12/2004 | Hickok et al. |
| 2005/0244341 | A1 | 11/2005 | Edwards et al. |
| 2006/0182716 | A1* | 8/2006 | Hong et al. ................... 424/85.6 |

FOREIGN PATENT DOCUMENTS

| EP | 813875 | 12/1997 |
|---|---|---|
| JP | 8119984 | 5/1996 |
| WO | WO 91/04748 | 4/1991 |
| WO | WO 91/08291 | 6/1991 |
| WO | WO 91/10727 | 7/1991 |
| WO | WO 92/00330 | 1/1992 |
| WO | WO 93/09228 | 5/1993 |
| WO | WO 93/09800 | 5/1993 |
| WO | WO 94/09812 | 5/1994 |
| WO | WO 94/10187 | 5/1994 |
| WO | WO 94/25588 | 11/1994 |
| WO | WO 95/10610 | 4/1995 |
| WO | WO 97/13844 | 4/1997 |
| WO | WO 97/40848 | 11/1997 |
| WO | WO 98/17304 | 4/1998 |
| WO | WO 98/48024 | 10/1998 |

(Continued)

OTHER PUBLICATIONS

Website:http://www.urmc.rochester.edu/encyclopedia/content.cfm?pageid=P02940 accessed Jun. 28, 2011.*

(Continued)

*Primary Examiner* — David Romeo
(74) *Attorney, Agent, or Firm* — Finnegan, Henderson, Farabow, Garrett & Dunner, LLP

(57) ABSTRACT

The disclosure relates to methods of treating an infant at risk of developing bronchopulmonary dysplasia, including premature infants, by administering a TGF-β antagonist during the perinatal period, including the prenatal period and/or the postnatal period. For administration during the prenatal period, the TGF-β antagonist can be administered either directly to the infant in utero, or indirectly by administration to the mother.

24 Claims, 13 Drawing Sheets

(56) References Cited

FOREIGN PATENT DOCUMENTS

| WO | WO 00/66631 | 11/2000 |
|----|----|----|
| WO | WO 02/062753 | 8/2002 |
| WO | WO 02/062776 | 8/2002 |
| WO | WO 02/062787 | 8/2002 |
| WO | WO 02/062793 | 8/2002 |
| WO | WO 02/062794 | 8/2002 |
| WO | WO 02/066462 | 8/2002 |
| WO | WO 02/094833 | 11/2002 |
| WO | WO 03/087304 | 10/2003 |
| WO | WO 03/097615 | 11/2003 |
| WO | WO 03/097639 | 11/2003 |
| WO | WO 2004/010929 | 2/2004 |
| WO | WO 2004/016606 | 2/2004 |
| WO | WO 2004/021989 | 3/2004 |
| WO | WO 2004/022054 | 3/2004 |
| WO | WO 2004/024159 | 3/2004 |
| WO | WO 2004/026302 | 4/2004 |
| WO | WO 2004/026871 | 4/2004 |
| WO | WO 2004/047818 | 6/2004 |
| WO | WO 2004/048381 | 6/2004 |
| WO | WO 2004/048382 | 6/2004 |
| WO | WO 2004/048930 | 6/2004 |
| WO | WO 2004/050659 | 6/2004 |
| WO | WO 2004/056352 | 7/2004 |
| WO | WO 2004/072033 | 8/2004 |
| WO | WO 2004/087056 | 10/2004 |
| WO | WO 2005/010049 A2 | 2/2005 |
| WO | WO 2005/032481 | 4/2005 |
| WO | WO 2005/065691 | 7/2005 |
| WO | WO 2005/092894 | 10/2005 |
| WO | WO 2005/097832 | 10/2005 |
| WO | WO 2005/101149 | 10/2005 |
| WO | WO 2006/026305 | 3/2006 |
| WO | WO 2006/026306 | 3/2006 |
| WO | WO 2006/052568 | 5/2006 |
| WO | WO 2006/086469 A2 | 8/2006 |

OTHER PUBLICATIONS

Definition: McGraw-Hill Concise Dictionary of Modern Medicine; preterm infant, 2002, retrieved Jun. 28, 2011; http://medical-dictionary.thefreedictionary.com/preterm+infant.*

MeSH Database, entry for "Bronchopulmonary Dysplasia" [online], NCBI, NLM, NIH, 45 Center Drive, Bethesda, MD 20892, USA. [retrieved on Dec. 13, 2012]. Retrieved from the Internet: <URL:http://www.ncbi.nlm.nih.gov/mesh?term=Bronchopulmonary%20Dysplasia>.*

WebMD, entry for "Lung Injuries", [online], [retrieved on Dec. 13, 2012]. Retrieved from the Internet: <URL: http://www.webmd.com/lung/lung-injuries>.*

International Search Report and Written Opinion of Application No. PCT/US2007/021234 mailed Apr. 15, 2008.

Sunday, M. et al. "Bombesin-like Petide Mediates Lung Injury in a Baboon Model of Bronchopulmonary Dysplasia" *Journal of Clinical Investigation*, 102(3): 584-594, Aug. 1998.

Toti, P. et al. "Bronchopulmonary Dysplasia of the Premature Baby: An Immunohistochemical Study" *Pediatric Pulmonology*, 24:22-28, 1997.

El-Gamel, A. et al. "Transforming Growth Factor Beta (TGF-β) and Obliterative Bronchiolitis Following Pulmonary Transplantation" *Journal of Heart and Lung Transplant*, 18(9): 828-837, 1999.

Kotecha, S. et al. "Increase in the Concentration of Transforming Growth Factor Beta-1 in Bronchoalveolar Lavage Fluid before Development of Chronic Lung Disease of Prematurity", *Journal of Pediatrics*, 128: 464-9, 1996.

Gauldie, J. et al. "Transfer of the Active Form of Transforming Growth Factor-β1 Gene to Newborn Rat Lung Induces Changes Consistent with Bronchopulmonary Dysplasia" *American Journal of Pathology*, 163:2575-2584, 2003.

Speer, C. P. "Inflammation and Bronchopulmonary Dysplasia" *Seminars in Neonatology*, 8:29-38, 2003.

Nakanishi, H. et al. "TGF-β-Neutralizing Antibodies Improve Pulmonary Alveologenesis and Vasculogenesis in the Injured Newborn Lung" *Am. J. Physiol. Lung Cell Mol. Physiol.*, 293: L151-L161, 2007.

Bonikos, "Oxygen Toxicity in the Newborn," Am. J. Pathol. 85:623-650 (1976).

Bourbon et al., "Control Mechanisms of Lung Alveolar Development and Their Disorders in Bronchopulmonary Dysplasia," Pediatric Research 57:38R-46R (2005).

Dasch et al., "Monoclonal antibodies recognizing transforming growth factor-β," J. Immunol. 142:1536-1541 (1989).

Demetriou et al., "Fetuin/α2-HS Glycoprotein is a Transforming Growth Factor-β Type II receptor Mimic and Cytokine Antagonist," J. Biol. Chem. 271:12755 (1996).

Fakhrai et al., "Eradication of established intracranial rat gliomas by transforming growth factor β antisense gene therapy," Proc. Nat. Acad. Sci. USA., 93:2909-2914 (1996).

Florini et al., "Transforming Growth Factor-β," J. Biol. Chem. 261:16509-16513 (1986).

Graham et al., "Localization of Transforming Growth Factor-β at the Human Fetal-Maternal Interface: Role in Trophoblast Growth and Differentiation," Biol. Reprod. 46:561-572 (1992).

Groneck et al., "Inflammatory mediators and bronchopulmonary dysplasia," Arch. Dis. Child Fetal Neonatal. Ed. 73:F1-3 (1995).

Hayes et al., "An β-$_D$-Galactosyl-binding Lectin from *Bandeiraea simplicifolia* Seeds," J. Biol. Chem., 249:1904-1914 (1974).

Holley et al., "Purification of kidney epithelial cell growth inhibitors," Proc. Natl. Acad. Sci. USA 77:5989-5992 (1980).

Jobe et al., "Bronchopulmonary Dysplasia," Am. J. Resp. Crit. Card. Med. 163:1723-1729 (2001).

Jobe et al., "Prevention of bronchopulmonary dysplasia," Curr. Opin. Pediatr. 13:124-129 (2001).

Kotecha, "Lung growth for beginners," Paediatr. Respir. Rev. 1:308-13 (2000).

Kucich et al., "Stabilization of Elastin mRNA by TGF-β: Initial Characterization of Signaling Pathway," Am. J. Respir. Cell Mol. Biol. 17:10-16 (1997).

Leask et al., "TGF-β signaling and the fibrotic response," Faseb J. 18:816-827 (2004).

Lecart et al., "Bioactive Transforming Growth Factor-Beta in the Lungs of Extremely Low Birthweight Neonates Predicts the Need for Home Oxygen Supplementation," Biol. Neonate 77:217-223 (2000).

Massaro et al., "Postnatal development of pulmonary alveoli: modulation in rats by thyroid hormones," Am. J. Physiol. 250:R51-55 (1986).

Massaro et al., "Retinoic Acid treatment partially rescues failed septation in rats and in mice," Am. J. Physiol. Lung Cell Mol. Physiol. 278:L955-60 (2000).

McMurty, "Introduction: pre- and postnatal lung development, maturation, and plasticity," Am. J. Physiol. Lung Cell Mol. Physiol. 282:L341-344 (2002).

Neptune et al., "Dysregulation of TGF-β activation contributes to pathogenesis in Marfan syndrome," Nat. Genet. 33:407-411 (2003).

Padela et al., "Hepatocyte Growth Factor is Requirement for Alveologenesis in the Neonatal Rat," Am. J. Respir. Crit. Care Med. 172:907-914 (2005).

Parks et al., "Posttranscriptional Regulation of Lung Elastin Production," Am. J. Respir. Cell Mol. Biol. 17:1-2 (1997).

Perkowski et al., "Gene Expression Profiling of the Early Pulmonary Response to Hyperoxia in Mice," Am. J. Respir. Cell Mol. Biol. 28:682-696 (2003).

Roberts et al., "New class of transforming growth factors potentiated by epidermal growth factor: Isolation from non-neoplastic tissues," Proc. Natl. Acad. Sci. USA 78:5339-5343 (1981).

Roberts et al., "Oxygen-Induced Alterations in Lung Vascular Development in the Newborn Rat," Pediatr. Res. 17:368-375 (1983).

Roberts et al., "Regulation of Endothelial Cell Growth, Architecture, and Matrix Synthesis by TGF-β," Am. Rev. Respir. Dis. 140:1126-1128 (1989).

Roberts et al., "Nitric Oxide Inhalation Decreases Pulmonary Artery Remodeling in the Inured Lungs of Rat Pups," Circ. Res. 87:140-145 (2000).

(56) References Cited

OTHER PUBLICATIONS

Ruzek et al., "Minimal Effects on Immune Parameters Following Chronic Anti-TGF-β Monoclonal Antibody Administration to Normal Mice," Immunopharmacol. Immunotoxicol. 25:235-257 (2003).
Saito et al., "Mitogenic Activity of Tracheal Effluents from Premature Infants with Chronic Lung Disease," Pediatr. Res. 55:960-965 (2004).
Seyedin et al., "Purification and characterization of two cartilage-inducing factors from bovine demineralized bone," Proc. Natl. Acad. Sci. USA 82:2267-2271 (1985).
Vicencio et al., "Conditional Overexpression of Bioactive Transforming Growth Factor β-1 in Neonatal Mouse Lung," Am. J. Respir. Cell Mol. Biol. 31:650-656 (2004).
Warner et al., "Functional and pathological effects of prolonged hyperoxia in neonatal mice," Am. J. Physiol. 275:L110-117 (1998).
Zhao et al., "Adenovirus-mediated decorin gene transfer prevents TGF-β-induced inhibition of lung morphogenesis," Am. J. Physiol., 21:L412-422 (1999).
Zhao et al., "Expression of transforming growth factor-β receptors during hyperoxia-induced lung injury and repair," Am. J. Physiol. 273:L355-362 (1997).
Zhao et al., "Ontogeny and localization of TGF-β type I receptor expression during lung development," Am. J. Physiol. Lung Cell Mol. Physiol. 278:L1231-1239 (2000).
Alejandre-Alcázar et al., "Hyperoxia modulates TGF-β/BMP signaling in a mouse model of bronchopulmonary dysplasia," *Am J Physiol Lung Cell Mol Physiol*, 292: L537-L549 (2007).
Bland et al., "Dysregulation of pulmonary elastin synthesis and assembly in preterm lambs with chronic lung disease," *Am J Physiol Lung Cell Mol Physiol*, 292: L1370-L1384 (2007).
Kunzmann et al., "Antenatal inflammation induced TGF-β1 but suppressed CTGF in preterm lungs," *Am J Physiol Lung Cell Mol Physiol*, 292: L223-L231 (2007).
Husain et al., "Pathology of Arrested Acinar Development in Postsurfactant Bronchopulmonary Dysplasia," *Hum. Pathol.*, 29:710-717 (1998).
Jobe et al., "Mechanisms initiating lung injury in the preterm," *Early Hum. Dev.*, 53:81-94 (1998).
Zhang et al., "TGFβ Mediates Hypoxia-Induced Inhibition of Alveolization in Newborn Mice," ESPR Abstracts, 59: 30-31 (2006).
R & D Systems, TGF-β1, 2, 3 Antibody Monoclonal Mouse IgG1, Clone #1D11, Catalog No. MAB1835, Mar. 4, 2011.
Charafeddine et al., "Atypical Chronic Lung Disease Patterns in Neonates," *Pediatrics*, 103: 759-765 (1999).
"Dysplasia," from *Dorland's Illustrated Medical Dictionary*, 31st Edition, Saunders Elsevier, Philadelphia, PA, pp. 587-589 (2007).
Giri et al., "Effect of antibody to transforming growth factor β on bleomycin induced accumulation of lung collagen in mice," *Thorax*, 48: 959-966 (1993).

\* cited by examiner

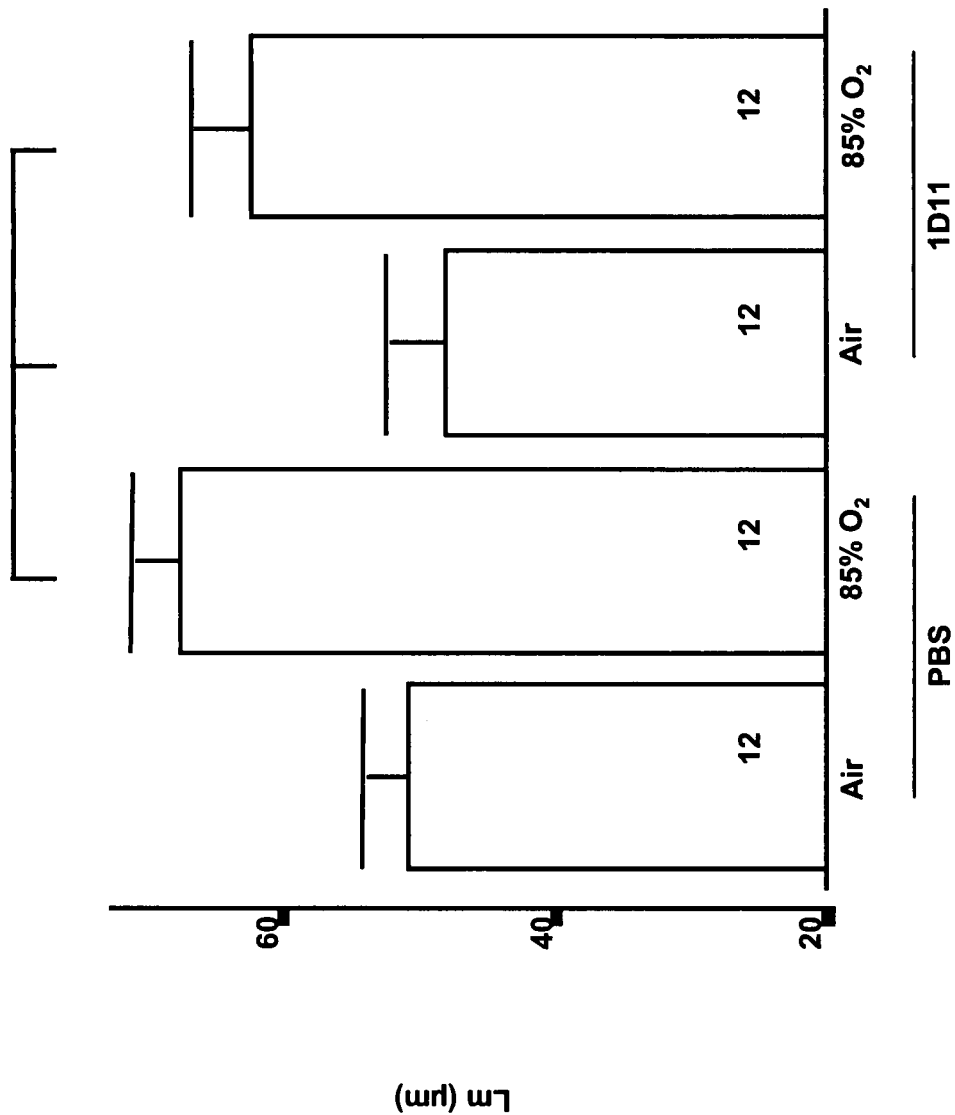

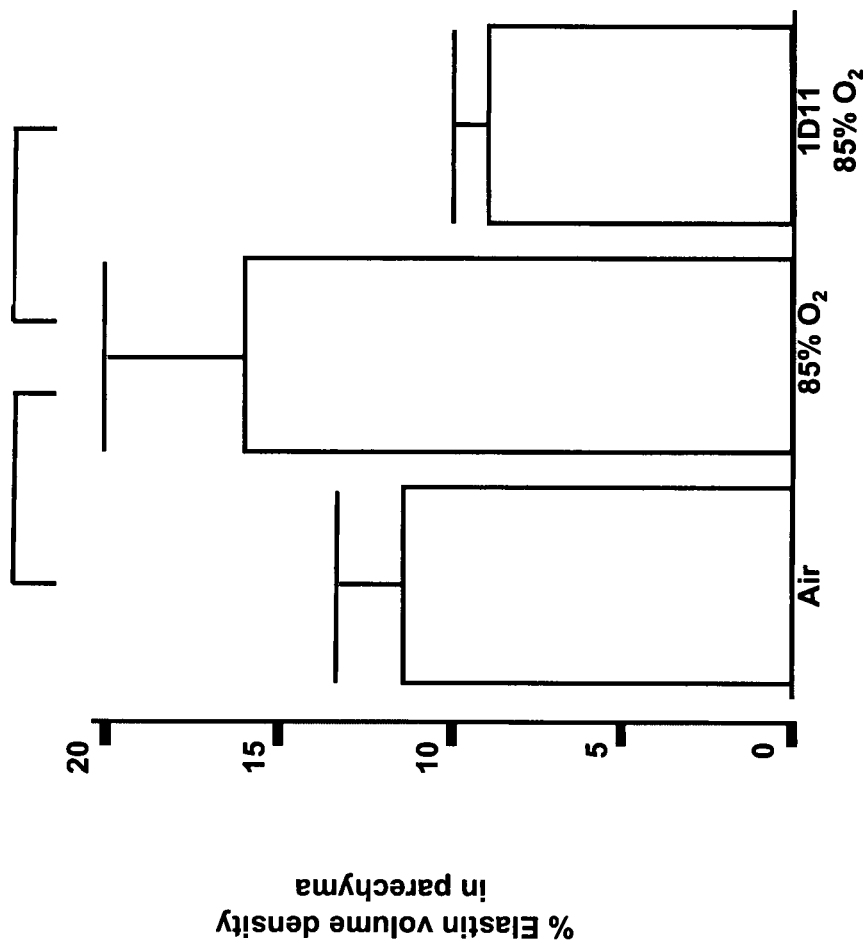

USE OF TGF-β ANTAGONISTS TO TREAT INFANTS AT RISK OF DEVELOPING BRONCHOPULMONARY DYSPLASIA

This application claims priority to U.S. Provisional Application No. 60/827,933, filed on Oct. 3, 2006, which is incorporated herein by reference in its entirety.

TECHNICAL FIELD

The invention relates to the use of TGF-β antagonists to treat infants at risk of developing bronchopulmonary dysplasia, including premature infants.

BACKGROUND

Infants born at a very early stage of development commonly suffer respiratory failure because of their immature lungs, primitive respiratory drive, and vulnerability to infection. Bronchopulmonary dysplasia (BPD), a chronic lung disease in premature infants, was first characterized almost 40 years ago (Northway, *N. Engl. J. Med.* 276:357-368 (1967); Jobe et al., *Am. J. Resp. Crit Card. Med.* 163:1723-1729 (2001)). As initially described, BPD was a condition that occurred primarily in infants who were of sufficient size and maturity to survive the ravages of prolonged exposure to high oxygen and positive-pressure ventilation. These were mainly infants born between 28 and 32 weeks gestation and who weighed between 1,000 and 1,500 grams at birth. Their clinical course and lung pathology reflected the consequences of severe pulmonary oxygen toxicity and lung overexpansion. The initial pathologic descriptions of BPD noted airway injury, inflammation, interstitial fibrosis, smooth muscle cell hyperplasia, and squamous metaplasia in the distal airways. Mortality among these infants was high, and long-term ventilator-dependent respiratory failure was common among survivors (Bland, *Biol. Neonate* 88:181-191 (2005)).

With the advent of surfactant therapy, the widespread use of antenatal steroid therapy, and the use of advanced ventilator and nutritional therapies, the epidemiology and pathophysiology of BPD have changed considerably. Now, almost two-thirds of infants who acquire BPD weigh less than 1,000 gm and are born before 28 weeks of gestation (Martinez et al., in *Chronic Lung Disease in Early Infancy*, pp. 21-39; New York, Marcel Dekker (2000); Bancalori et al., *Id.* at pp. 41-64). In contrast to past experience, when pulmonary oxygen toxicity and lung overexpansion were considered major contributors to the development of chronic lung injury, premature infants developing BPD now are exposed to lower levels of oxygen and mechanical ventilation.

In addition, the lung pathology of these extremely immature infants with BPD differs from the "classic form" of BPD. Sometimes referred to as the "new BPD," the disease primarily is now associated with disrupted terminal lung development. Microscopic inspection of the lungs of babies who have, died from BPD reveals a partial to complete arrest in distal lung development (Husain et al., *Hum. Pathol* 29:710-717 (1998)). This results in peripheral lung units of babies with BPD that have reduced alveologenesis and diminished and dysmorphic microvasculature development.

Development of the pulmonary air sacs is crucial for extrauterine survival. Lung development can be divided into five overlapping stages: early embryonic (3-7 weeks of gestation), pseudoglandular (5-17 weeks of gestation), canalicular (16-26 weeks of gestation), saccular (24-38 weeks of gestation) and alveolar (36 weeks of gestation to 2 years of postnatal age) (Burri, in *Lung Growth and Development*, ed. J. McDonald, pp. 1-35; New York, Marcel Dekker (1997); Kotecha, *Paediatr. Respir. Rev.* 1:308-13 (2000); Coalson, *Sem. in Neonatology* 8:73-81 (2003)). For infants born at 26 weeks gestation, the saccular and alveolar stages are not complete. During the saccular stage, the walls of the lung saccules thin, and secondary crests within the wall form. The tremendous expansion of the prospective respiratory airspaces causes the formation of saccules and a marked decrease in the interstitial tissue mass. The lung looks more and more "aerated," although it is filled with fluid originating from the lungs and from the amniotic fluid surrounding the fetus. During the alveolar stage, alveolar formation begins by an extension and thinning of the secondary crests as they mature into the walls of alveoli. Thus, alveologenesis commences after birth for most preterm infants.

Although the mechanisms causing BPD are not completely known, indirect evidence suggests that BPD results from the effects of cytokines on the developing lung (Groneck et al., *Arch. Dis. Child Fetal Neonatal. Ed.* 73:F1-3 (1995); Jobe et al., *Early Hum. Dev.* 53:81-94 (1998); Jobe et al., *Curr. Opin. Pediatr.* 13:124-129 (2001)). For example, intrauterine infections have been observed to increase the levels of cytokines in the lungs of premature newborns and to be associated with an increased risk for BPD. In addition, exposure of the premature lung to oxygen and ventilator therapies has been associated with an increase in cytokine levels in pulmonary effluents and with an increased risk for developing BPD. Furthermore, it is possible that there are direct genetic causes for BPD. Because several genes are thought to be critical for terminal lung development (Bourbon et al., *Pediatric Research* 57:38R-46R (2005)), it is possible that abnormalities in one or more of them could directly inhibit normal lung maturation and cause BPD. Moreover, it is also possible that genetic abnormalities may indirectly increase the incidence of BPD by causing premature delivery.

Recent, limited indirect evidence suggests that TGF-β may be one of the numerous cytokines involved in inhibition of terminal lung development in BPD. For example, TGF-β has been identified in the terminal airways and pulmonary effluents of premature babies (Kotecha et al., *J. Pediatr.* 128:464-469 (1996); Toti et al., *Pediatr. Pulmon.* 24:22-28 (1997); Lecart et al., *Biol. Neonate* 77:217-223 (2000); Saito et al., *Pediatr. Res.* 55:960-965 (2004)), and the level of TGF-β1 is greatest in preterm babies who develop BPD (Kotecha, 1996) and correlates with the severity of the illness (Lecart, 2000). However, it remains unknown whether this reported increase in TGF-β levels is merely a consequence of the activity of other factors that are primarily responsible for the disease, or whether TGF-β plays a more direct role in the development of BPD. For example, besides TGF-β, approximately 20 candidate genes have been identified so far that might control terminal lung development. Of these genes, 13 have been reported to be modulated in animal models or infants with BPD (Bourbon et al., *Pediatr. Res.* 57:38R-46R (2005)). Using gene expression profiling techniques, Perkowski and coworkers reported that 385 genes are modulated during hyperoxic lung injury in the adult mouse (*Am. J. Respir. Cell Mol. Biol.* 28:682-696 (2003)).

At least two studies have examined the effect of ectopic overexpression of TGF-β1 in the developing lung. For example, Vicencio et al. reported that overexpression of biologically active TGF-β1 in the lung epithelium of newborn mice was associated with inhibition of terminal lung development (*Am. J. Respir. Cell Mol. Biol.* 31:650-656 (2004)), and Gauldie et al. reported that infection of newborn rat lungs with an adenovirus encoding TGF-β1 affected newborn lung structure, including producing patchy areas of fibrosis (which are not seen in the new BPD). (*Am. J. Pathol.* 163:2575-2584 (2003)). However, it is unclear whether the changes observed in this later model were directly related to the activity of TGF-β1, because the control lungs exposed to adenovirus (without TGF-β) exhibited marked distal airway edema, suggesting the adenovirus vector itself induced inflammation. Moreover, both studies involve forced ectopic expression of TGF-β, and therefore do not model what occurs during injury to the developing lung in premature infants with BPD. Thus, these studies are not helpful in elucidating the role of TGF-β in BPD.

At the same time, other studies have suggested that TGF-β regulates early events in lung development, including branching morphogenesis (Zhao et al., *Am. J. Physiol.* 273:L355-362 (1997); Zhao et al., *Am. J. Physiol.* 21:L412-422 (1999)). However, branching morphogenesis of the fetal lung, which affects the numbers of conducting proximal airways, is completed, prior to the saccular stage of lung development (McMurty, *Am. J. Physiol. Lung Cell Mol. Physiol.* 282:L341-344 (2002)). Thus, defects in branching morphogenesis are associated with diseases of early lung development, such as lung hypoplasia and congenital diaphragmatic hernia, but not of BPD, a disease of inhibition or disruption of the saccular and alveolar phases of lung development. Because abnormalities in branching morphogenesis are not observed in the lungs of infants with BPD, where the number of conducting proximal airways is normal, these studies also are not helpful in elucidating whether TGF-β plays a role in the pathogenesis of BPD.

Finally, the effect of TGF-β neutralization on lung development has been investigated in certain models of pediatric lung diseases, but not in BPD. In these cases, TGF-β activity was increased in the normal lung by alterations in the binding of TGF-β to extracellular matrix (Neptune et al., *Nat. Genet.* 33:407-411 (2003) and Massaro et al., *Am. J. Physiol. Lung Cell Mol. Physiol.* 278:L955-60 (2000)) or supplying excess levels to fetal lungs growing in culture (Zhang et al., *E-PASS*2006 59:5166.6 (2006)). Whether neutralization of excess TGF-β produced in the injured developing lung inhibited development of BPD was not investigated. Due to differences in etiology, pathology and disease course, these investigations in which TGF-β was neutralized have not contributed to our understanding of the role of TGF-β in BPD. See, for example, Neptune et al., *Nat. Genet.* 33:407-411 (2003) and Massaro et al., *Am. J. Physiol. Lung Cell Mol. Physiol.* 278:L955-60 (2000), which reported on the role of abnormal TGF-β signaling in mouse models of Marfan's disease; and Zhang et al., *E-PASS*2006 59:5166.6 (2006), which reported on the role of TGF-β in hypoxic mice that are models of congenital heart disease or of pulmonary vascular diseases associated with living in high altitudes.

In summary, while some studies have suggested that TGF-β is capable of affecting terminal lung development, others have suggested that TGF-β plays a role at a much earlier stage, during branching morphogenesis, and no studies have ever directly addressed whether TGF-β plays a causative role in modulating terminal lung development in the injured lung of a premature infant at risk of developing BPD, or whether neutralization of TGF-β would have any impact on the course of disease in such infants.

BPD is an extremely important cause of infant morbidity and mortality. Behind asthma, BPD is the most costly disease of pediatric patients. The availability of surfactant therapy and other advances in treatment have improved neonatal survival without associated reduction in rates of BPD. Therefore, there exists an important need for improved methods to treat premature infants at risk of developing BPD.

SUMMARY

The present invention is based, in part, on the discovery and demonstration that administration of an anti-TGF-β antibody during the perinatal period protects the injured developing lung from inhibition of alveologenesis and vasculogenesis in a hyperoxic mouse model of bronchopulmonary dysplasia. The invention provides methods of treating infants who are at risk of developing bronchopulmonary dysplasia (BPD), including premature infants.

The present invention provides methods of treating an infant by administering a TGF-β antagonist during the perinatal period, including the prenatal period and/or the postnatal period. For administration during the prenatal period, the TGF-β antagonist can be administered either directly to the infant in Utero, or indirectly by administration to the mother.

In one embodiment, methods of the invention involve treating premature infants at risk for developing bronchopulmonary dysplasia, wherein the age of the infant is about 24 weeks gestation about 6 months after birth. In one embodiment, the infant to be treated is a premature infant born at about 32 weeks gestation or younger. In one embodiment, the infant to be treated is a premature infant born at about 28 weeks gestation or younger. In one embodiment, the weight of the infant at birth is about 1500 grams or less. In another embodiment, the weight of the infant at birth is about 1000 grams or less.

In another embodiment, methods of the invention involve treating prematurely born newborns and infants with lung injury and bronchopulmonary dysplasia, wherein the age of the infant is to about 6 months after birth with TGF-β neutralizing agents to decrease the severity of disease.

In some embodiments, the TGF-β antagonist is a direct TGF-β antagonist, such as, for example, an anti-TGF-β antibody, an anti-TGF-β receptor antibody, or a soluble TGF-β receptor. In specific embodiments, the TGF-β antagonist is a human or humanized form of the anti-TGF-β antibody 1D11. In nonlimiting embodiments, the TGF-β antagonist is a human pan-specific antibody such as PET1073G12, PET1074B9 or PET1287A10, as disclosed in PCT application WO 06/086469.

The TGF-β antagonist can be administered systemically, including intramuscularly, intravenously, or subcutaneously. The TGF-β antagonist can also be administered directly to the lung in an aerosolized form, including via an inhaler or a nebulizer, as droplets or in powder form, or with surface active carriers.

In some embodiments, the TGF-β antagonist can be used to manufacture a medicament for treating bronchopulmonary dysplasia. Further, in some embodiments, the medicament can include a TGF-β antagonist and another therapeutic agent including, for example, a steroid, vitamin A, high calorie nutritional formulation, a diuretic, and/or a bronchodilator.

In other embodiments, the TGF-β antagonist can increase alveologenesis in the developing lungs of an infant. In some embodiments, the increased alveologenesis and/or vasculogenesis can be in the peripheral lungs. In some embodiments, the TGF-β antagonist can be administered to decrease the mean cord length of the infants lungs by at least about 10%, by at least about 20%, by at least about 30%, or by at least about 40%. In other embodiments, the TGF-β antagonist can be administered to decrease the alveolar volume density by at least about 20%, by at least about 30%, by at least about 40%, at least about 50%, or by at least about, 60%. Further, in one embodiment, the TGF-β antagonist can be administered to increase the secondary septal density by at least about 20%, by at least about 30%, by at least about 40%, or by at least about 50%.

In some embodiments, the TGF-β antagonist can be administered to produce more normal lung structure. For example, in one embodiment, TGF-β antagonist can be administered to decrease elastin volume density. Further, in other embodiments, the TGF-β antagonist can be administered to increase vasculogenesis in developing lungs of an infant. For example, in one embodiment, the TGF-β antagonist can be administered to increase elastin and/or αSMA expression in peripheral lung tissue.

In another embodiment, the TGF-β antagonist can be administered to treat or prevent injury due to oxygen supplementation. For example, in one embodiment, the TGF-β antagonist can be administered before, or in conjunction with, oxygen supplementation to prevent or treat abnormal lung development due to chronic oxygen exposure and/or lung overinflation. In one embodiment, the TGF-β antagonist can be administered in utero or shortly after birth of the infant, and the oxygen therapy can be administered after birth. Further, in another embodiment, the TGF-β antagonist can be administered to encourage normal growth of the infant after birth.

DESCRIPTION OF THE FIGURES

In FIGS. 2A-2C, TGF-β immunoreactivity (dark staining) was detected in 10 day-old mouse pup lungs using 1D11, a pan-specific monoclonal anti-TGF-β antibody. In FIGS. 2D-2F, lungs were incubated with non-immune serum instead of 1D11. As shown in FIG. 2A, TGF-β immunoreactivity was identified in cells in the walls of large airways (*) and vessels (**) and in the extracellular matrix (arrow). TGF-β immunoreactivity was also identified in the distal airways of the pup lung (FIGS. 2B and 2C). All panels were counterstained with hematoxylin. Closed scale bars: 20 μm; open scale bars: 50 μm.

FIGS. 5A-5C are graphical representations of experiments, which show that in the injured lung, treatment with anti-TGF-β antibody improved objective, quantitative indices of alveolar development. In the PBS-treated mouse lung, chronic exposure to 85% oxygen was associated in the peripheral lung with an increase in mean chord length (Lm) (FIG. 5A) and the airspace volume density (% AVD) (FIG. 5B), which are inversely proportional to peripheral lung development and airway surface area, and a decrease the secondary septal density in the developing lung (FIG. 5C). Treatment with 1D11 inhibited the abnormal increase of Lm and % AVD and improved the density of secondary septae in lungs chronically exposed to high levels of $O_2$. N=12 each group; *P<0.05.

FIG. 6B). Treatment with anti-TGF-β antibodies was associated with improved deposition of elastin in the tips of alveolar septae. Closed scale bar: 100 μm; open scale bar: 20 μm.

FIG. 7A is a photomicrograph and FIG. 7B is a graphical representation of experiments that demonstrate that treatment of the injured developing lung with anti-TGF-β antibody improved the % elastin volume density in the peripheral lung parenchyma (% EVD), which is an objective, quantitative index of extracellular matrix development. In the PBS-treated mouse lung, chronic exposure to 85% oxygen was associated with abnormal elastin deposition as reflected by an increase in % EVD. Treatment with 1D11 inhibited the abnormal increase in the % EVD by improving elastin organization in the peripheral lung. N=4 each group; *P<0.05.

DETAILED DESCRIPTION

Figure 1:
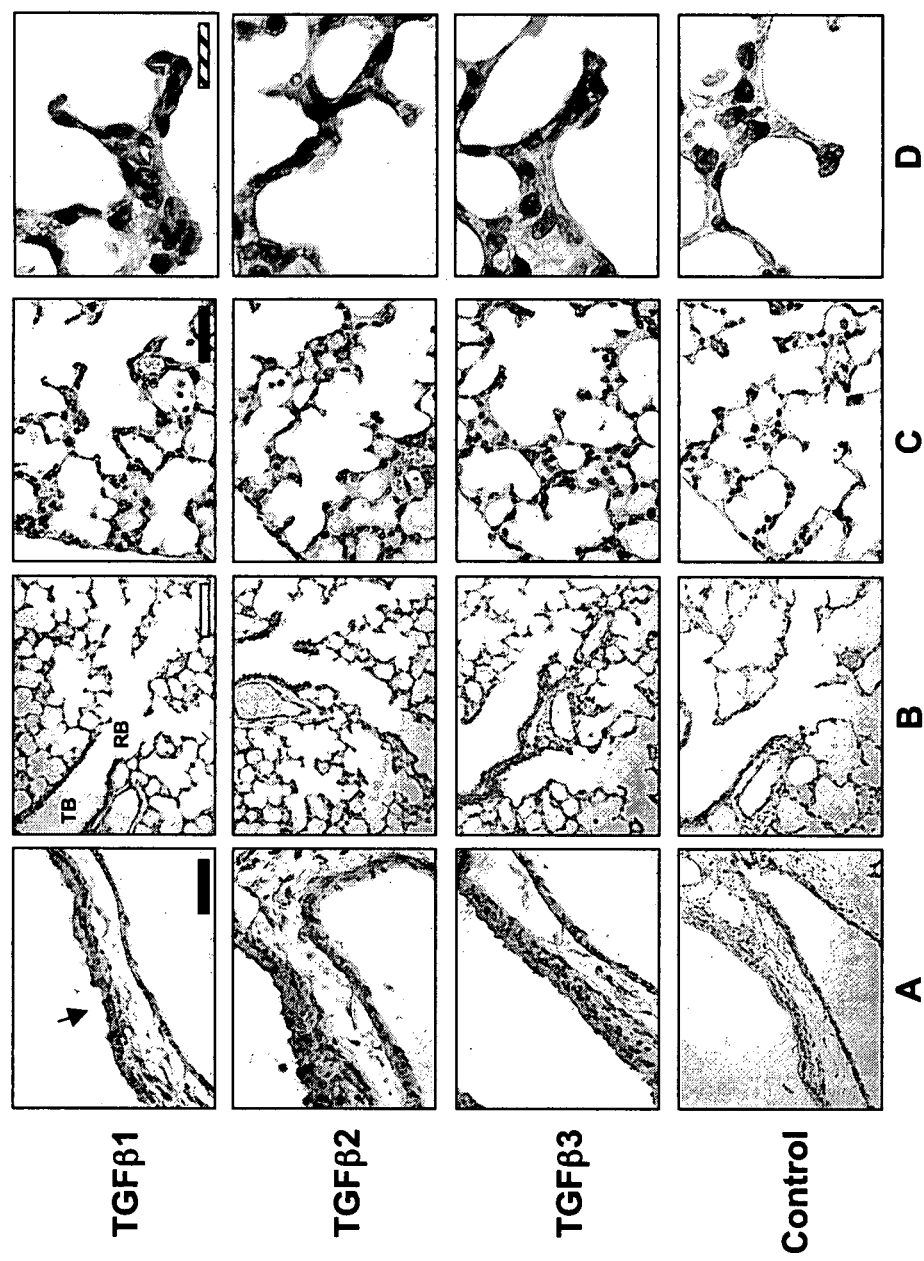
FIGS. 1A-1D are photomicrographs, which show that TGF-β isoforms are expressed in the developing mouse pup lung. Differential TGF-β immunoreactivity (dark staining) was detected in the bronchial epithelium (FIG. 1A; arrow), terminal and respiratory bronchioles (FIG. 1B; TB and RB, respectively), and in the terminal airways (FIG. 1C and FIG. 1D) of 10 day-old mouse pup lungs. In addition, there appeared to be more abundant TGF-β1 immunoreactivity in the walls of the terminal airway in comparison with TGF-β2 and TGF-β3. All panels are counterstained with hematoxylin. Closed scale bar: 50 μm; open scale bar: 100 μm; crosshatched scale bar 30 μm.

The present invention provides methods of treating infants, including premature infants at risk of developing bronchopulmonary dysplasia (BPD), or have already developed BPD, at at least one point during the perinatal period, including the prenatal period and the postnatal period, by administering a therapeutically effective amount of a TGF-β antagonist to the infant in the perinatal period, including the prenatal period and the postnatal period. As used herein, the term "infant" includes humans at approximately 24 weeks gestation, either in utero or after birth, up to about 6 months after birth.

Bronchopulmonary Dysplasia

The clinical diagnosis of BPD is made in any prematurely born infant who, at 36 weeks gestation, has lung disease requiring continuous or continual supplemental oxygen and who has had an abnormal chest X-ray. As used herein, "BPD" also includes all alternative clinical diagnosis definitions, such as a diagnosis in infants older than four weeks from birth who have had persistent lung disease requiring continual supplemental oxygen and who have had abnormal chest X-rays. BPD is also sometimes referred to in the literature and by pediatric caretakers as "chronic lung disease" (Jobe et al., *Early Hum. Devel.* 53:81-94 (1998)).

Because BPD clinically is not diagnosed in prematurely born infants until some time after birth, e.g. 36 weeks gestation, therapies to treat at-risk infants are typically administered before the disease is formally diagnosed. In some methods, therapies are used to treat infants who have been diagnosed with BPD to lessen the severity of the disease. According to the methods of the invention, TGF-β antagonists are used to treat infants during the perinatal period. As used herein, the "perinatal period" in humans for treatment using the methods of the invention includes both the prenatal period (i.e. before birth) as well as the postnatal period (i.e. after birth), and starts from about 26 weeks gestation and continues to about 6 months after birth. For administration during the prenatal period, the TGF-β antagonist can be administered either directly to the fetus in utero, or indirectly by administration to the mother.

In certain methods of the invention, the TGF-β antagonist is administered in a therapeutically effective amount to treat an infant at risk of developing BPD, and thereby reduce, minimize, or prevent the development of BPD in the infant. As used herein, the term "treat" is used to mean to act upon to reduce, minimize, or prevent the pulmonary sequelae and clinical signs and symptoms that are associated with BPD. Infants who can be treated with the methods of the invention include any infants at risk of developing BPD. Infants at risk of developing BPD include premature infants, infants at risk for premature delivery, and any other infants at risk of developing BPD for other reasons.

The age of the infants to be treated with the methods of the invention are from about 24 weeks gestation to about 6 months after birth. The number of weeks gestation (i.e., gestational age) can be determined using any of a number of conventional methods. For example, the gestational age can be calculated from the first day of the last menstruation.

In one embodiment, the infant is a premature infant. As used herein, a premature infant is any infant born before 37 weeks gestation; the term "preterm delivery" or "premature delivery" refers to any delivery that occurs before 37 weeks gestation. Thus, in one embodiment, the at-risk infant to be treated is a premature infant (born before 37 weeks gestation) whose age is at least 24 weeks gestation.

Almost two-thirds of infants who acquire BPD weigh less than 1,000 grams and are less than 28 weeks gestation at birth. Accordingly, in one embodiment, the infants to be treated with the TGF-β antagonists can be identified by their weight and/or age at birth. In one embodiment, the infant to be treated is a premature infant born at about 32 weeks gestation or younger. In one embodiment, the infant to be treated is a premature infant born at about 28 weeks gestation or younger. In one embodiment, the infant to be treated weighs about 1500 grams or less at birth. In another embodiment, the infant weighs about 1000 grams or less at birth.

Infants at risk of developing BPD also include yet to be born infants (i.e. fetuses) at risk for premature delivery (and therefore at risk for BPD). Such infants are treated during the prenatal period, either by administration to the mother or direct administration to the fetus in utero. Any pregnant woman at about 23 or more weeks gestation with clinically intact membranes and having one or more risk factors for preterm delivery or preterm delivery markers may be a candidate for treatment.

A large number of factors are known to be associated with the risk of preterm delivery. These factors include, but are not limited to, multiple fetus gestations; incompetent cervix; uterine anomalies; polyhydramnios; nulliparity; previous preterm rupture of membranes or preterm labor; preeclampsia; vaginal bleeding associated with placental previa; little or no antenatal care; and symptoms such as abdominal pain, low backache, passage of cervical mucus and contractions.

In addition to these risk factors, a number of preterm delivery markers have been identified. As used herein, a preterm delivery marker is a marker that, when present at or beyond a threshold level, indicates an increased risk of preterm delivery. Examples of preterm delivery markers include, but are not limited to, fetal restricted antigens such as fetal fibronectin and estriol (U.S. Patent Application Publication No. 2004/0266025), insulin-like growth factor binding protein 1 (a marker for the likelihood of membrane rupture; see U.S. Patent Application Publication No. 2004/0053838), and MMP-8 and MMP-9 (U.S. Patent Application Publication No. 2004/0029176). Methods to detect the level of preterm delivery markers are well known in the art, and described, for example, in U.S. Patent Application Publication No. 2004/0266025.

Although BPD is seen mostly among premature babies, it can also occur in full-term babies who have respiratory problems during their first days of life. Accordingly, the methods of the invention can be used to treat these infants as well.

TGF-β Antagonists

TGF-β is a disulfide-linked dimer that is synthesized as a preproprotein of about 400 amino acids (aa) that is cleaved prior to secretion to produce mature TGF-β. The N-terminal cleavage fragment, known as the "latency-associated peptide" (LAP), may remain noncovalently bound to the dimer, thereby inactivating TGF-β. TGF-β, isolated in vivo, is found predominantly in this inactive, "latent" form, i.e., associated with LAP. Latent TGF-β complex may be activated in several ways, for example, by binding to a cell surface receptor called the cation-independent mannose-6-phosphate/insulin-like growth factor 11 receptor. Binding occurs through mannose-6-phosphate residues attached at glycosylation sites within LAP. Upon binding to the receptor, TGF-β is released in its mature form. Mature, active TGF-β is then free to bind to its receptor and exert its biological functions. The major TGF-β-binding domain in the type 11 TGF-β receptor has been mapped to a 19 amino acid sequence (Demetriou et al., *J. Biol. Chem.* 271:12755 (1996)).

The term "TGF-β," as used herein, refers to any one or more mammalian isoforms of TGF-β. Likewise, the term "TGF-β receptor," unless otherwise indicated, refers to any receptor that binds at least one mammalian TGF-β isoform. Currently, there are five known isoforms of TGF-β (TGF-β1 to TGF-β5), all of which are homologous among each other (60-80% identity), form homodimers of about 25 kDa, and act upon common TGF-β receptors (TβR-I, TβR-II, TβR-IIB, and TβR-III). TGF-β1, TGF-β2, and TGF-β3 are found in mammals. The structural and functional aspects of TGF-β, as well as TGF-β receptors, are well known in the art (see, for example, Cytokine Reference, eds. Oppenheim et al., Academic Press, San Diego, Calif., 2001). TGF-β is remarkably conserved among species. For example, the amino acid sequences of rat and human mature TGF-β1s are nearly identical. Thus, antagonists of TGF-β are expected to have a high species cross-reactivity.

The term "TGF-β antagonist" and its cognates such as "inhibitor," "neutralizing," and "downregulating" refer to a compound (or its property as appropriate), or other molecule, which acts as an antagonist of the biological activity of TGF-β. A TGF-β antagonist may, for example, bind to and neutralize the activity of TGF-β; decrease TGF-β expression levels; affect the stability or conversion of the precursor molecule to the active, mature form; interfere with the binding of TGF-β to one or more receptors; or it may interfere with intracellular signaling of a TGF-β receptor. The term "direct TGF-β antagonist" generally refers to any compound that directly downregulates the biological activity of TGF-β. A molecule "directly downregulates" the biological activity of TGF-β if it downregulates the activity by interacting with a TGF-β gene, a TGF-β transcript, a TGF-β ligand, or a TGF-β receptor.

Methods for assessing the biological activity of TGF-β, including the neutralizing activity of TGF-β antagonists, are known in the art. Examples of some of the more frequently used in vitro bioassays include the following:

(1) induction of colony formation of NRK cells in soft agar in the presence of EGF (Roberts et al., *Proc. Natl. Acad. Sci. USA* 78:5339-5343 (1981));

(2) induction of differentiation of primitive mesenchymal cells to express a cartilaginous phenotype (Seyedin et al., *Proc. Natl. Acad. Sci. USA* 82:2267-2271 (1985));

(3) inhibition of growth of Mv1Lu mink lung epithelial cells (Danielpour et al. (1989) *J. Cell. Physiol.*, 138:79-86) and BBC-1 monkey kidney cells (Holley et al., *Proc. Natl. Acad. Sci. USA* 77:5989-5992 (1980));

(4) inhibition of mitogenesis of C3H/HeJ mouse thymocytes (Wrann et al. (1987) *EMBO J.*, 6:1633-1636);

(5) inhibition of differentiation of rat L6 myoblast cells (Florini et al., *J. Biol. Chem.* 261:16509-16513 (1986));

(6) measurement of fibronectin production (Wrana et al., *Cell* 71:1003-1014 (1992));

(7) induction of plasminogen activator inhibitor I (PAI-1) promoter fused to a luciferase reporter gene (Abe et al. (1994) *Anal. Biochem.*, 216:276-284);

(8) measurement of PAI-1 levels in lung tissue or the serum or plasma;

(9) sandwich enzyme-linked immunosorbent assays (Danielpour et al., *Growth Factors* 2:61-71 (1989)); and

(10) cellular assays described in Singh et al., *Bioorg. Med. Chem. Lett.* 13 (24)'4355-4359 (2003)).

Examples of methods that may be used to assess TGF-β activity in vivo include assessment of SMAD2 phosphorylation and/or nuclear localization.

Examples of TGF-β antagonists that may be used include but are not limited to monoclonal and polyclonal antibodies directed against one or more isoforms of TGF-β (U.S. Pat. No. 5,571,714; WO 97/13844; and WO 00/66631; WO 05/097832; WO 05/101149; WO 06/086469); dominant negative and soluble TGF-β receptors or antibodies directed against TGF-β receptors (Flavell et al., *Nat. Rev. Immunol.* 2:46-53 (2002); U.S. Pat. No. 5,693,607; U.S. Pat. No. 6,001,969; U.S. Pat. No. 6,008,011; U.S. Pat. No. 6,010,872; WO 92/00330; WO 93/09228; WO 95/10610; and WO 98/48024; LAP (WO 91/08291); LAP-associated TGF-β (WO 94/09812); TGF-β-binding glycoproteins/proteoglycans such as fetuin (U.S. Pat. No. 5,821,227); decorin, betaglycan, fibromodulin, lumican, and endoglin (U.S. Pat. No. 5,583,103; U.S. Pat. No. 5,654,270; U.S. Pat. No. 5,705,609; U.S. Pat. No. 5,726,149; U.S. Pat. No. 5,824,655; U.S. Pat. No. 5,830,847; U.S. Pat. No. 6,015,693; WO 91/04748; WO 91/10727; WO 93/09800; and WO 94/10187); mannose-6-phosphate or mannose-1-phosphate (U.S. Pat. No. 5,520,926); prolactin (WO 97/40848); insulin-like growth factor 11 (WO 98/17304); extracts of plants, fungi, and bacteria (EU 813875; JP 8119984; and U.S. Pat. No. 5,693,610); antisense oligonucleotides (U.S. Pat. No. 5,683,988; U.S. Pat. No. 5,772,995; U.S. Pat. No. 5,821,234; U.S. Pat. No. 5,869,462; and WO 94/25588); and any mutants, fragments, or derivatives of the above-identified molecules that retain the ability to inhibit the biological activity of TGF-β. Numerous small molecule TGF-β antagonists that may be useful are also well known to those of skill in the art, including, but not limited to, those described in WO 02/62753; WO 02/62776; WO 02/62787; WO 02/62793; WO 02/62794; WO 02/66462; WO 02/94833; WO 03/87304; WO 03/97615; WO 03/97639; WO 04/10929; WO 04/21989; WO 04/22054; WO 04/24159; WO 04/26302; WO 04/26871; U.S. Pat. No. 6,184,226; WO 04/16606; WO 04/47818; WO 04/48381; WO 04/48382; WO 04/48930; WO 04/50659; WO 04/56352; WO 04/72033; WO 04/87056 WO 05/10049; WO 05/032481; WO 05/065691; WO 05/92894; WO 06/026305; WO 06/026306; and WO 06/052568.

In some embodiments, the TGF-β antagonist is a direct TGF-β antagonist, for example, an antibody that blocks TGF-β binding to its receptor.

The term "antibody," as used herein, refers to an immunoglobulin or a part thereof, and encompasses any polypeptide comprising an antigen-binding site regardless of the source, method of production, and other characteristics. The term includes, but is not limited to, polyclonal, monoclonal, monospecific, polyspecific, humanized, human, single-chain, chimeric, synthetic, recombinant, hybrid, mutated, and CDRgrafted antibodies. The term "antigen-binding domain" refers to the part of an antibody molecule that comprises the area specifically binding to or complementary to, a part or all of an antigen. Where an antigen is large, an antibody may only bind to a particular part of the antigen. The "epitope," or "antigenic determinant" is a portion of an antigen molecule that is responsible for specific interactions with the antigen-binding domain of an antibody. An antigen-binding domain may comprise an antibody light chain variable region ($V_L$) and an antibody heavy chain variable region ($V_H$). An antigen-binding domain may be provided by one or more antibody variable domains (e.g., an Fd antibody fragment consisting of a $V_H$ domain, an Fv antibody fragment consisting of a $V_H$ domain and a $V_L$ domain, or an scFv antibody fragment consisting of a $V_H$ domain and a $V_L$ domain joined by a linker). The term "anti-TGF-β antibody," or "antibody against at least one isoform of TGF-β," refers to any antibody that specifically binds to at least one epitope of TGF-β. The terms "TGF-β receptor antibody" and "antibody against a TGF-β receptor" refer to any antibody that specifically binds to at least one epitope of a TGF-β receptor (e.g., type I, type II, or type III).

Antibodies useful in the methods of the invention specifically bind to at least one isoform of TGF-β or to the extracellular domain of at least one TGF-β receptor. The terms "specific interaction," or "specifically binds," or their cognates, as used herein, mean that two molecules form a complex that is relatively stable under physiologic conditions. Specific binding is characterized by a high affinity and a low to moderate capacity. Nonspecific binding usually has a low affinity with a moderate to high capacity. Typically, the binding is considered specific when the affinity constant $K_a$ is higher than $10^6$ $M^{-1}$; or preferably higher than $10^8$ $M^{-1}$.

In some other embodiments, the anti-TGF-β antibody specifically binds at least one isoform of TGF-β selected from the group consisting of TGF-β1, TGF-β2, and TGF-β3. In yet other embodiments, the anti-TGF-β antibody specifically binds to at least: (a) TGF-β1, TGF-β2, and TGF-β3 ("pan-neutralizing antibody"); (b) TGF-β1 and TGF-β2; (c) TGF-β1 and TGF-β3; or (d) TGF-β2 and TGF-β3. In various embodiments, the affinity constant $K_a$ of the TGF-β antibody for at least one isoform of TGF-β, which it specifically binds, is preferably greater than $10^6$ $M^{-1}$, $10^7$ $M^{-1}$, $10^8$ $M^{-1}$, $10^9$ $M^{-1}$, $10^{10}$ $M^{-1}$, $10^{11}$ $M^{-1}$, or $10^{12}$ $M^{-1}$. Also contemplated for use in humans are humanized and fully human forms and derivatives of nonhuman antibodies that neutralize one or more isoforms of mammalian TGF-β. Producing such antibodies is well within the ordinary skill of an artisan (see, e.g., Antibody Engineering, ed. Borrebaeck, 2nd ed., Oxford University Press (1995)). In nonlimiting illustrative embodiments, the anti-TGF-β antibody is the murine monoclonal antibody 1D11 produced by the hybridoma 1D11.16 (Deposited at the American Type Culture Collection (ATCC) at 10801 University Boulevard, Manassas, Va., 20110, United States of America, ATCC Deposit Designation No. HB 9849, so described in U.S. Pat. Nos. 5,571,714; 5,772,998; and 5,783,185). The sequence of the 1D11 heavy chain variable region is available under accession No. AAB46787. Thus, in related embodiments, the anti-TGF-β antibody is a derivative of 1D11, e.g., an antibody comprising CDR sequences identical to heavy chain CDRs in AAB46787, such as a humanized antibody. In further embodiments, the anti-TGF-β antibody is a human antibody isolated from a phage display library using guided selection from 1D11.

In nonlimiting embodiments, the anti-TGF-β antibody is a human pan-specific antibody such as PET1073G12, PET1074B9, or PET1287A10, as disclosed in PCT application WO 06/086469.

Methods of Administration

Using the teachings provided herein and the abundance of information in the art regarding the characteristics, including potencies and affinities, of various TGF-β antagonists, a skilled clinician may readily determine the exact dosages and regimens for any given TGF-β antagonist. For example, where the TGF-β antagonist is an antibody, it may be administered at a dose selected to provide the same neutralizing potency as the 1D11 antibody at a dose of 0.1 to 10 mg/kg body weight of the patient. Similarly, a therapeutically effective dose of an anti-TGF-β receptor antibody, a soluble TGF-β receptor, or another TGF-β antagonist may be selected in a range that would give comparable neutralizing potencies. In general, higher dosages may be administered to the mother to achieve effective dosages of the TGF-β antagonist in the fetus; lower dosages of the TGF-β antagonist may be administered for direct delivery to the lungs of the fetus or infant.

"Administration" is not limited to any particular formulation, delivery system, or route and may include, for example, parenteral (including subcutaneous, intravenous, intramedullary, intraarticular, intramuscular, or intraperitoneal injection) rectal, topical, transdermal, or oral (for example, in capsules, suspensions, or tablets). Administration to an individual may occur in a single dose, bolus dose, or in repeat administrations, and in any of a variety of pharmaceutical compositions containing physiologically acceptable salt forms, and/or with an acceptable pharmaceutical carrier and/or additive as part of a pharmaceutical composition. Physiologically acceptable salt forms and standard pharmaceutical formulation techniques and excipients are known (see, e.g., Physicians' Desk Reference® 2003, 57th ed., Medical Economics Company, 2002; and Remington: The Science and Practice of Pharmacy, eds. Gennado et al., 20th ed, Lippincott, Williams & Wilkins, 2000).

In one embodiment, administration of compositions comprising a TGF-β antagonist can be via a pulmonary route, including in the form of an inhalant as a powdered or liquid aerosol. Aerosolized formulations can be droplets or powder particles less than 10 μm in diameter. For example, the antagonist can be solubilized in a micronized hydrophobic/hydrophilic emulsion. Such inhalants may be administered by nebulizer, inhaler, intratracheal routes, intraoral or intranasal routes. Aerosols for the delivery of therapeutic agents to the respiratory tract, including aerodynamically light particles, are described, for example, in U.S. Patent Application Publication No. 2005/0244341.

Administration of an antagonist to an infant may also be accomplished by means of gene therapy, wherein a nucleic acid sequence encoding the antagonist is administered to the patient in vivo or to cells in vitro, which are then introduced into a patient, and the antagonist (e.g., antisense RNA, snRNA, soluble TGF-β receptor) is expressed from an appropriate nucleic acid vector sequence. Methods for gene therapy delivery of TGF-β antagonists are described (see, e.g., Fakhrai et al., Proc. Nat. Acad. Sci. U.S.A., 93:2909-2914 (1996)) and U.S. Pat. No. 5,824,655. Administration of a TGF-β antagonist is effected by gene transfer using a vector comprising cDNA encoding the antagonist, for example cDNA encoding the extracellular domain of TGF-β type II (rsTGF-BIIR) or type III receptor (rsTGFBIIIR), as described in, e.g., U.S. Patent Application Publication No. 2003/0180301.

The TGF-β antagonist can be administered to the infant in combination with any other agents or therapies that are currently used or will be used to treat premature infants at risk for or diagnosed with BPD. Poor vitamin A status during the first month of life significantly increases the risk of developing BPD. Studies have also found that dexamethasone can increase plasma levels of vitamin A; which can help wean infants off oxygen therapy, thereby preventing BPD.

Bronchodilator medications are often used to open the airways of the lungs by relaxing the muscles around the airways. Anti-inflammatory medications are used to reduce airway swelling in more severely ill babies whose wheezing and respiratory distress are occasionally difficult to control with bronchodilators only. Accordingly, treatments for BPD that may be used in combination with the methods of the invention include surfactant, oxygen therapy, ventilator therapy, steroids, vitamin A, inhaled nitric oxide, high calorie nutritional formulations, intravenous feeding, antibiotics, fluid restriction and diuretics to decrease water accumulation in the lungs, and physical therapy to improve muscle performance and to help the lungs expel mucus.

The following examples provide illustrative embodiments. One of ordinary skill in the art will recognize the numerous modifications and variations that may be performed without altering the spirit or scope of the present invention. Such modifications and variations are encompassed within the scope of the invention. The examples do not in any way limit the invention.

EXAMPLES

Experimental Design.

On embryonic days 17 and 19, time-dated pregnant C57BL/6 mice (Charles River) were treated with i.p. injections of 0.5 ml of PBS pH 7.4 with or without 10 mg/kg of 1D11 (Genzyme), a pan-specific anti-TGF-β $IgG_1$ antibody, or an isotype-matched myeloma protein without known antigen (MOPC21; Sigma-Aldrich). Within 12 hours of birth, the pups of pairs of similarly treated mothers were pooled and randomly divided into two litters that were subsequently treated continuously, with their mothers, with either air or 85% oxygen for 10 days. Every 24 hours, the nursing mothers from paired litters were exchanged between the $O_2$ exposure levels to diminish the effects of breathing high levels of $O_2$. Medical grade oxygen and nitrogen gases (Airgas) were blended using separately regulated and calibrated flow meters. The gas mixtures were introduced into a 680 L acrylic exposure chamber. An airlock permitted the exchange of the mothers and the freshening of food, water, and bedding without changing the pup oxygen exposure level. The fresh gas flow rate in the exposure chamber exceeded the calculated oxygen consumption of the mice within it by >10-fold (Bartlett et al., *Respir. Physiol.* 29:193-200 (1997)). The oxygen level was measured using paramagnetic methods (Servomex model 572). This exposure method produced a gaseous atmosphere with stable oxygen levels with relative humidity and temperature in the exposure chamber that did not exceed 60% and 70° C., respectively. All protocols were approved by the Subcommittee for Research Animal Studies of the Massachusetts General Hospital.

Tissue Preparation.

To obtain lungs and hearts for analysis, pups were weighed and sacrificed by i.p. injection of 200 mg/kg sodium pentobarbital. A thoracotomy was made to permit the lungs to collapse, the trachea was identified through a transverse incision in the neck, and a 0.61 mm O.D. polyethylene tube (PE10; Harvard Apparatus) was secured in the trachea. Lungs were inflated with 3% paraformaldehyde and 0.1% gluteraldehyde in PBS at 22 cm $H_2O$ pressure for 30 minutes, followed by ligation of the airways while the lungs were distended. Pup bodies were submerged in fixative for 3 days at 4° C. Hearts and lungs were dissected from the bodies and stored at 4° C. in PBS for further analysis. To obtain pulmonary tissue for frozen sectioning, the tracheae were cannulated, and lungs were gently distended with Tissue Freezing Medium (TFM; Triangle Biochemical Sciences) and 20% sucrose in PBS (diluted 1:1 by vol) and removed. Subsequently, the lungs were covered with TFM, frozen in isopentane (kept on dry ice), and stored at −80° C. until use.

Detection of Tissue TGF-β.

TGF-β isoform immunoreactivity was detected in pup lungs using immunohistochemistry. Following citrate acid antigen retrieval, lung sections were blocked and exposed to rabbit anti-TGF-β1 (Santa Cruz, sc-146), TGF-β2, (sc-90), and TGF-β3 (sc-82) antibodies and to pre-immune rabbit serum (control). After extensive washing, the sections were exposed to biotinylated anti-rabbit antibody, avidin-biotin-peroxidase complexes (Vector Labs) and diaminobenzidine (DAB; Vector labs) before being counterstained with hematoxylin. Pulmonary TGF-β was also detected using a pan-specific anti-TGF-β antibody and indirect immunohistochemistry (Graham et al., *Biol. Reprod.* 46:561-572 (1992)) and a commercially available kit optimized for the use of murine antibodies in mouse tissues (M.O.M. Immunodetection kit; Vector Labs). Paraffin-embedded lung sections, 6 μm-thick, were treated with xylene, graded alcohol solutions, and hydrated in PBST (PBS containing 0.1% Tween 20). After incubation in blocking reagent, the tissue was exposed to 1D11 (diluted in blocking solution) overnight at 4° C. After washing the tissue with PBST, it was incubated with a biotinylated anti-mouse antibody, washed with PBST, and exposed to avidin-biotin-peroxidase complexes (Vector Labs) and diaminobenzidine (DAB; Vector labs) before counterstaining with hematoxylin.

Analysis of TGF-β Signaling.

Nuclear phospho-SMAD 2 (p-Smad2) was detected in the lungs using indirect immunohistochemistry. Frozen lung sections, 6 μm-thick, were placed on Superfrost Plus™ glass slides (Fisher Scientific), fixed with 4% paraformaldehyde in PBS for 2 minutes, and permeabilized with 100% methanol for 10 minutes. After blocking with 5% goat serum in PBST for 1 hour, sections were exposed to rabbit anti-pSmad2 (Cell Signaling) diluted in blocking buffer overnight at 4° C. After washing the sections with PBST, they were incubated with a biotinylated anti-rabbit antibody, washed with PBST, and exposed to avidin-biotin peroxidase complexes and DAB before counterstaining with hematoxylin.

Stereological Analysis of Lung Structure.

Lung pathophysiology was characterized by determining lung volume, Lm (the mean linear intercept or chord length), and % AVD (% airspace volume density). Lung volumes were determined using the Archimedes principle after inflation-fixation of lungs. Injured developing lungs have interrupted alveolarization and remain in a saccular-like developmental stage, with distal airways with increased diameters. These changes are quantified using stereologic methods and by determining Lm (Massaro et al., *Am. J. Physiol.* 250:R51-55 (1986); Tomkeieff, *Nature* 155:24 (1945)), % AVD (Weibel, *Stereological methods*. London: Academic Press (1979)), and secondary septal density (Pierce et al. *Am J Physiol.* 272: L452-60 (1997)). The Lm is inversely proportional to the internal surface area of the lung (Thurlbeck, *Am. Rev. Respir. Dis.* 95:752-764 (1967); Thurlbeck, *Am. Rev. Respir. Dis.*

95:765-773 (1967)). The secondary septal density directly correlates with alveolar development.

Inflation-fixed pup lungs were embedded in methyl methacrylate, and 2 µm-thick, toluidine blue-stained sections of the left lung were used for structural studies. While obtaining and processing the pulmonary image data, the observer was masked to the treatment group and exposures of the lung. Using a systematic sampling approach (similar to the approach of Tschanz and Burri, *Exp. Lung Res.* 28:457-471 (2002)), four 0.60 mm$^2$ fields from randomly oriented, transverse sections of the left lungs that excluded large airway and vascular structures were digitized for the determination of Lm; within these fields, four 0.15 mm$^2$ sections were captured for determination of % AVD. Using a custom-written macro and ImageJ (Rasband, ImageJ, Bethesda, Md. (1997-2004)), images were filtered and segmented using previously described methods (Tschanz et al., 2002). To determine Lm, images were inverted and merged using a bit-wise logical AND operation with an image containing horizontal lines 90 µm apart. The resulting chords were ordered; chords <8 µm and >250 µm were discarded to remove those associated with pulmonary capillaries and conducting airways from the data (Soutiere et al., *Respir. Physiol. Neurobiol* 140:283-291 (2004)). Lm was determined by dividing the sum of the resulting chords by the number of intercepts. The % AVD of the distal airspace was determined using standard point-counting methods (Weibel, 1979). The secondary septal density was objectively determined by counting.

Lung Staining for Extracellular Matrix Proteins.

Lung elastin and collagen were determined using 6 µm-thick paraffin-embedded lung sections. Elastin staining was performed following treatment with 0.5% potassium permanganate and 1% oxalic acid, using Miller's elastin stain (Miller, *Stain Techno.* 28:148-149 (1971)). Collagen staining was performed using 0.1% Sirius red in saturated picric acid (Walsh et al., *Anal. Biochem.* 203:187-190 (1992)). The % elastin volume density in the parenchyma was determined using a standard method (Pierce et al. *Am J Physiol.* 272: L452-60 (1997)).

Evaluation of Vascular Development.

Lectin staining was used to identify the pulmonary microvasculature in the wall of the distal airways. Lectins from *Griffania (Bandeiraea) simplicifolia* have been observed to bind to α-D-galactosides (Hayes et al., *J. Biol. Chem.* 249:1904-1914 (1974)) in endothelial cells (Mattsson et al, *Pancreatology* 2:155-162 (2002)) and to preferentially identify the pulmonary microvasculature (King et al., *Microvasc. Res.* 67:139-151 2004)). Paraffin-embedded lung sections 6 µm-thick were blocked and incubated overnight with a biotinylated IB4 isoform of *G. simplicifolia* lectin (Molecular Probes). After washing with Tris-buffered saline containing 0.1% Tween 20 (TBST), bound lectin was detected using avidin-biotin complexed alkaline phosphatase and Vector Red substrate (Vector Laboratories), and sections were counterstained with toluidine blue. A murine monoclonal anti-αSMA antibody (1A4; Sigma) was used for immunohistochemistry to identify smooth muscle cells using 6 µm-thick, paraffin-embedded lung sections, as previously described (Roberts et al., *Circ. Res.* 87:140-145 (2000)).

The areal density of the pulmonary microvascular cells in the mouse pup lungs was analyzed using methods described by Weibel (1979). Sections of lungs reacted with biotinylated lectin and αSMA antibody and Vector Red substrate, as described above, were used to detail the endothelial and SMC compartments of the microvasculature, respectively. Using the systematic sampling method detailed above, epifluorescent images were obtained of the peripheral lung avoiding the pleura and large airway and vascular structures. After using filtration and segmentation procedures, the % fluorescent volume density (% FVD) was determined by dividing the number of pixels corresponding to fluorescent pixels by the total number in the image. The median % FVD of three images per pup lung section was used in the analysis.

The effect of chronically breathing 85% $O_2$ or air on right ventricular hypertrophy for 14 mouse pups was assessed by determining the Fulton ratio (Fulton et al., *Br. Heart J.* 14:413-420 (1952)). Following fixation in 3% paraformaldehyde and 0.1% gluteraldehyde in PBS for three days, hearts were stored in PBS at 4° C. The atria and large vessels were removed, and the right ventricular free wall was dissected from the left ventricle and interventricular septum. After blotting excess PBS from the tissue, the right ventricle and left ventricle (with septum) were weighed separately using a protected scale.

Statistical Methods.

The sample size for the stereologic analysis was determined using methods described by Pocock (Pocock, pp. 123-141 in *Clinical trials: A practical approach*, New York: John Wiley & Sons (1983)). Six lungs per group were studied to detect a possible decrease of Lm by 10%, using the isotypic control antibody with an α of 0.05 and power of 0.9. Preliminary studies indicated that treatment with 1D11 decreased the Lm of PBS-treated mice that breathed 85% $O_2$ from 68.0 to 62.3 µm, with a pooled SD of 4.2. Since these data indicated that 11.4 pup lungs per group would be required to demonstrate a salutary effect of 1D11 with an α of 0.05 and power of 0.90, 12 pup lungs were studied per treatment and exposure group. Pup weights in paired litters were analyzed using a randomized complete block design (Snedecor et al., pp. 255-273 in *Statistical Methods*, Ames, Iowa: Iowa State University Press (1980)). Data are presented as mean±SD and compared using a factorial model of ANOVA. When significant differences were detected, a Sheffe test was used post hoc. Significance was determined at P<0.05.

Example 1

Figure 2:
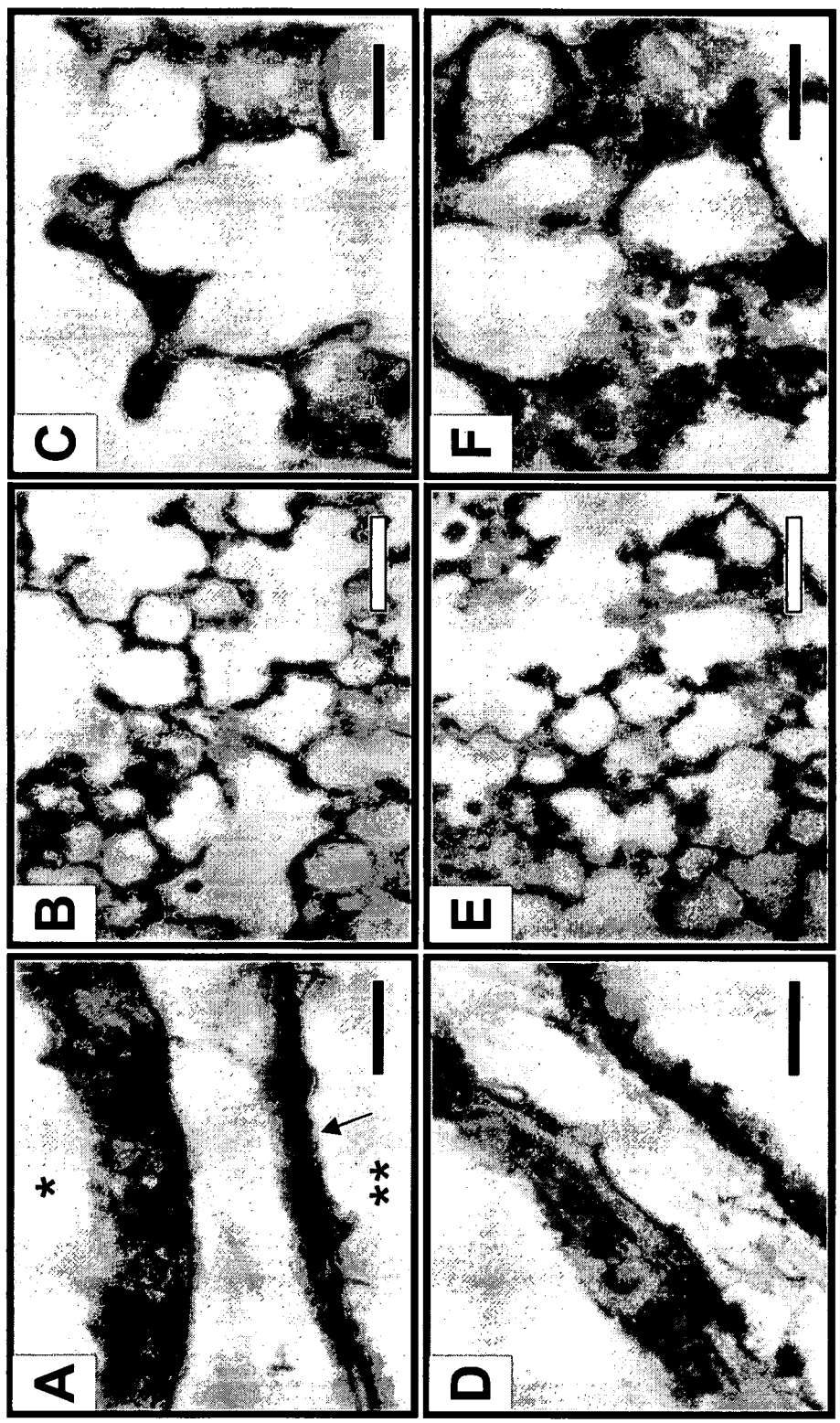
FIGS. 2A-2F are photomicrographs, which show that a TGF-β neutralizing antibody detects TGF-β expression in the 10 day-old mouse pup lung.

Expression of TGF-β In the Developing Lung and the Modulation of TGF-β Signaling with Anti-TGF-β Antibodies Although TGF-β1 and TGF-β2 RNA levels are observed to increase in the post-natal rat lung (Zhao et al., *Am. J. Physiol. Lung Cell Mol. Physiol.* 278:L1231-1239 (2000)), the TGF-β isoform expression pattern in the periphery of the developing lung largely is unknown. As shown in FIG. 1, TGF-β1-3 immunoreactivity is detected in the lungs of 10 day-old mouse pups. Similar TGF-β isoform levels are observed in the large conducting airways and in the terminal and respiratory bronchioles. Although TGF-β1 appears to have the highest immunoreactivity in the peripheral lung, TGF-β2 and TGF-β3 are detected there as well. Because it is desirable to determine whether inhibition of TGF-β activity in the distal developing lung inhibits the effects of lung injury on alveolar development, we first tested whether a pan-specific TGF-β neutralizing antibody recognizes TGF-β in the peripheral lung. 1D11 is a monoclonal antibody produced by a hybridoma generated from the splenocytes of Balb/c mice immunized with native bovine TGF-β2 (Dasch et al., *J. Immunol.* 142:1536-1541 (1989)). 1D11 neutralizes TGF-β1-3 in vitro (Dasch, 1989; Ruzek et al., *Immunopharmacol. Immunotoxicol* 25:235-257 (2003)) and identifies TGF-β in human placenta and decidual tissues (Graham et al., *Biol. Reprod.* 46:561-572 (1992)). As shown in FIG. 2, 1D11 detected TGF-β in the 10 day-old mouse lung. In particular, TGF-β immunoreactivity was observed in the walls of large and small airways and blood vessels. Intense extracellular TGF-β immunoreactivity was also associated with the extracellular matrix (arrow).

Figure 3:
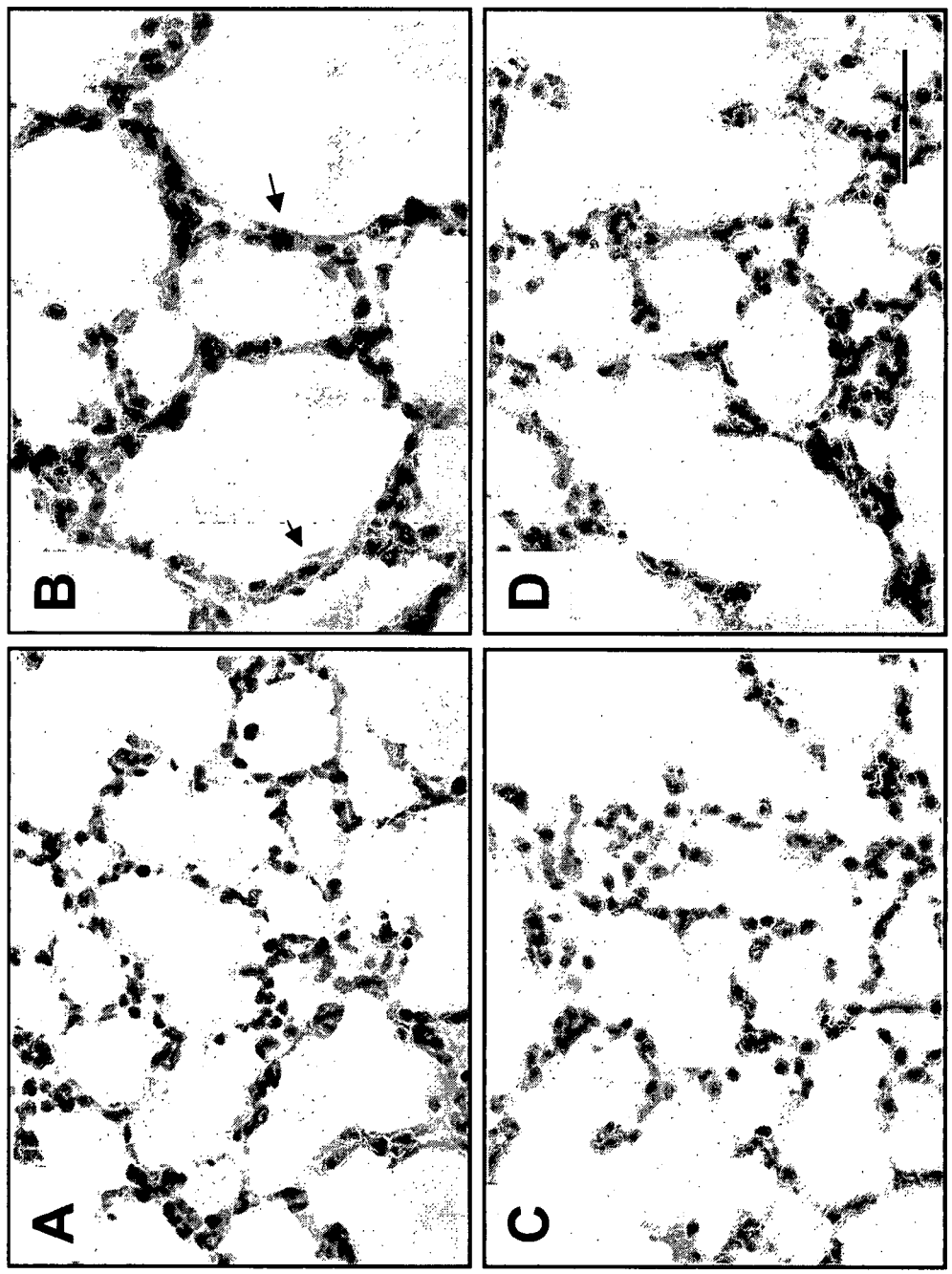
FIGS. 3A-3D are photomicrographs, which show that treatment with anti-TGF-β antibodies decreases TGF-β signaling in the injured newborn lung. Immunohistochemistry was used to detect p-Smad2 (dark staining) in the lungs of 10 day-old pups treated with: PBS and air (FIG. 3A), PBS and 85% $O_2$ (FIG. 3B), 1D11 and air (FIG. 3C), and 1D11 and 85% $O_2$ (FIG. 3D). Compared with air-exposed lungs, those treated with PBS and exposed to 85% $O_2$ for 10 days had more abundant p-Smad2 detected in the nuclei of distal airway cells (arrows indicate representative nuclear p-Smad2 immunoreactivity). In contrast, 1D11-treated $O_2$-exposed lungs had fewer nuclei with p-Smad2 reactivity than those treated with PBS and exposed to $O_2$. The 1D11-treated, $O_2$-exposed lungs also had a similar number of p-Smad2 stained nuclei as the lungs treated with PBS and 1D11 and exposed to air. All panels were counterstained with hematoxylin. Scale bar: 50 μm.

Although antenatal exposure to TGF-β neutralizing antibodies can inhibit TGF-β signaling in mice with abnormalities in the extracellular matrix (Neptune et al., 2003), it is unknown whether this approach can modulate an anticipated increase in TGF-β signaling in the injured developing lung. Since increased TGF-β signaling is associated with an increase in the phosphorylation and nuclear localization Smad2 or 3 (Nakao et al., *Embo J.* 16:5353-62 (1997)), immunohistochemistry was used to test whether hyperoxic pulmonary injury is associated with an increase in the nuclear compartmentalization of phosphorylated Smad2 (p-Smad2) in the mouse pup lung. Using this method, additional studies were performed to determine whether the increase in TGF-β signaling could be modified by treatment with anti-TGF-β antibodies. As shown in FIG. 3, in comparison with pup lungs treated with PBS and exposed to air, the level of nuclear p-Smad2 is increased in those treated with PBS and chronically exposed to 85% $O_2$. Importantly, 1D11 treatment was associated with a decrease in p-Smad2 nuclear localization in the pup lungs exposed to high levels of oxygen. These observations indicate that hyperoxic lung injury increases TGF-β signaling and that the excessive TGF-β activity can be attenuated with TGF-β neutralizing antibodies. It is also interesting to note that some of the pulmonary cells in PBS-treated air-exposed lungs have nuclear p-Smad2. This suggests that TGF-β has some basal activity in the post-natal lung and may play a role in regulating normal terminal lung development.

Example 2

Figure 4:
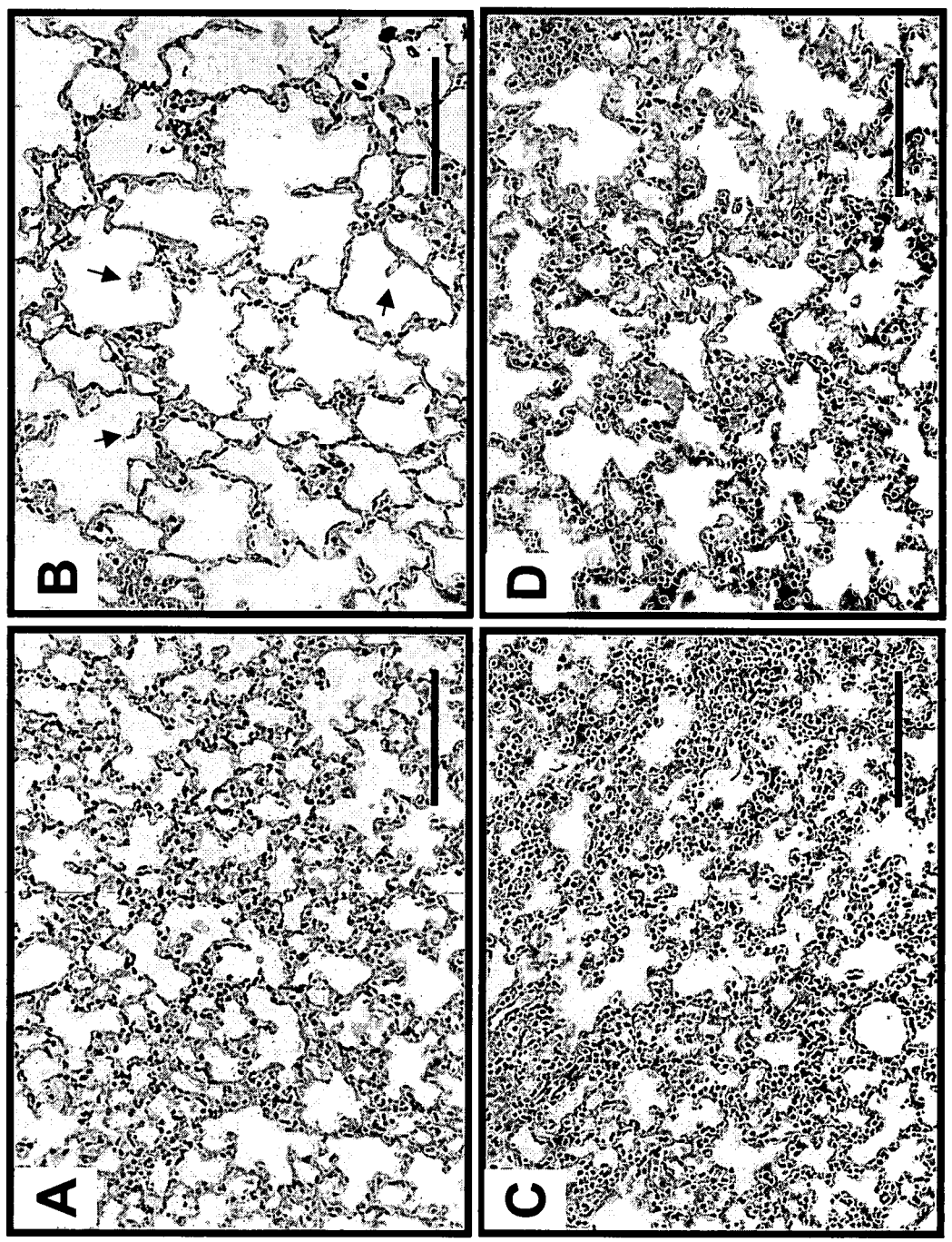
FIGS. 4A-4D are photomicrographs, which show anti-TGF-β antibody exposure was associated with improved distal airway development in the injured newborn lung. Toluidine blue was used to stain sections of lungs of 10 day-old pups treated with: PBS and air (FIG. 4A), PBS and 85% $O_2$ (FIG. 4B), 1D11 and air (FIG. 4C), and 1D11 and 85% $O_2$ (FIG. 4D). Treatment with PBS and exposure to 85% $O_2$ was associated with increased distal airspace area and decreased numbers of secondary septae (arrows) in comparison with lungs from air exposed pups. Treatment with 1D11 improved distal airway development in $O_2$-exposed pup lungs; there appeared to be more alveolar formation in these lungs. Scale bars: 200 μm.

Alveologenesis is Improved in the Injured Newborn Lung by Anti-TGF-β Antibody Treatment Chronic inhalation of high levels of oxygen by newborn rodents causes lung injury and inhibits terminal pulmonary development in a manner similar to that observed in infants with BPD (Bonikos et al., *Lab Invest.* 32:619-635 (1975); Frank et al., *J. Appl. Physiol.* 45:699-704 (1978); Pappas et al., *Lab Invest.* 48:735-748 (1983); Bonikos, *Am. J. Pathol.* 85:623-650 (1976); Warner et al., *Am. J. Physiol.* 275:L110-117 (1998)). Therefore, the hyperoxic mouse pup model of lung injury was used to test whether treatment with TGF-β neutralizing antibodies improves alveolar development. Exposure of newborn mouse pups to continuous 85% $O_2$ for 10 days was used because this level of exposure was observed in preliminary studies to cause diminished pulmonary alveologenesis while permitting a survival rate >80%. As shown in FIG. 4, chronic exposure to 85% $O_2$ was associated with a decrease in terminal lung development. The distal airways of the injured pup lung exhibited a less complex interstitial structure and fewer secondary septae and alveoli (arrows) in comparison with the lungs of air-breathing control pups. This increase in distal airspace area likely resulted from a decrease in interstitial tissue because the overall lung volume of the 85% $O_2$-exposed lungs was not different from that of those exposed to air (Lung volume, μl/g body weight: PBS and 85% $O_2$ 62±8 vs. PBS and air: 60±5. P>0.05).

Importantly, exposure to anti-TGF-β antibody improved terminal pulmonary development in the injured newborn lung since it led to a level of peripheral lung septation and airspace area that is closer to that observed in the PBS-treated air-breathing control lungs. In addition, exposure to 1D11 did not appear to be associated with lung toxicity. In the 1D11-treated and air-exposed lungs, there was not an important level of inflammatory cell infiltration in the distal airways. These observations suggest that attenuation of abnormal TGF-β signaling improves distal pulmonary development in the injured newborn mouse lung.

The effect of 1D11 on Lm and % AVD was examined in pup lungs exposed to 85% $O_2$ to determine whether treatment with anti-TGF-β antibodies improves alveologenesis in the injured newborn lung. The decrease in alveologenesis in the injured newborn lung has been associated with a reduction of internal pulmonary surface area and an increase in alveolar airspace area, which can be quantified by stereologic methods (Weibel, 1979; Bolender et al., *Am. J. Physiol.* 265:L521-548 (1993)). For example, Lm is inversely proportional to the internal lung surface area and % AVD inversely correlates with the alveolar airspace area. Others have reported that hyperoxic lung injury increases Lm and % AVD in the developing mouse and rat lung (Shaffer et al., *Pediatr. Res.* 21:14-20 (1987); Boros et al., *Am. J. Physiol.* 272:L433-441 (1997); Warner et al., *Am. J. Physiol.* 275:L110-117 (1998)).

Figure 5B:
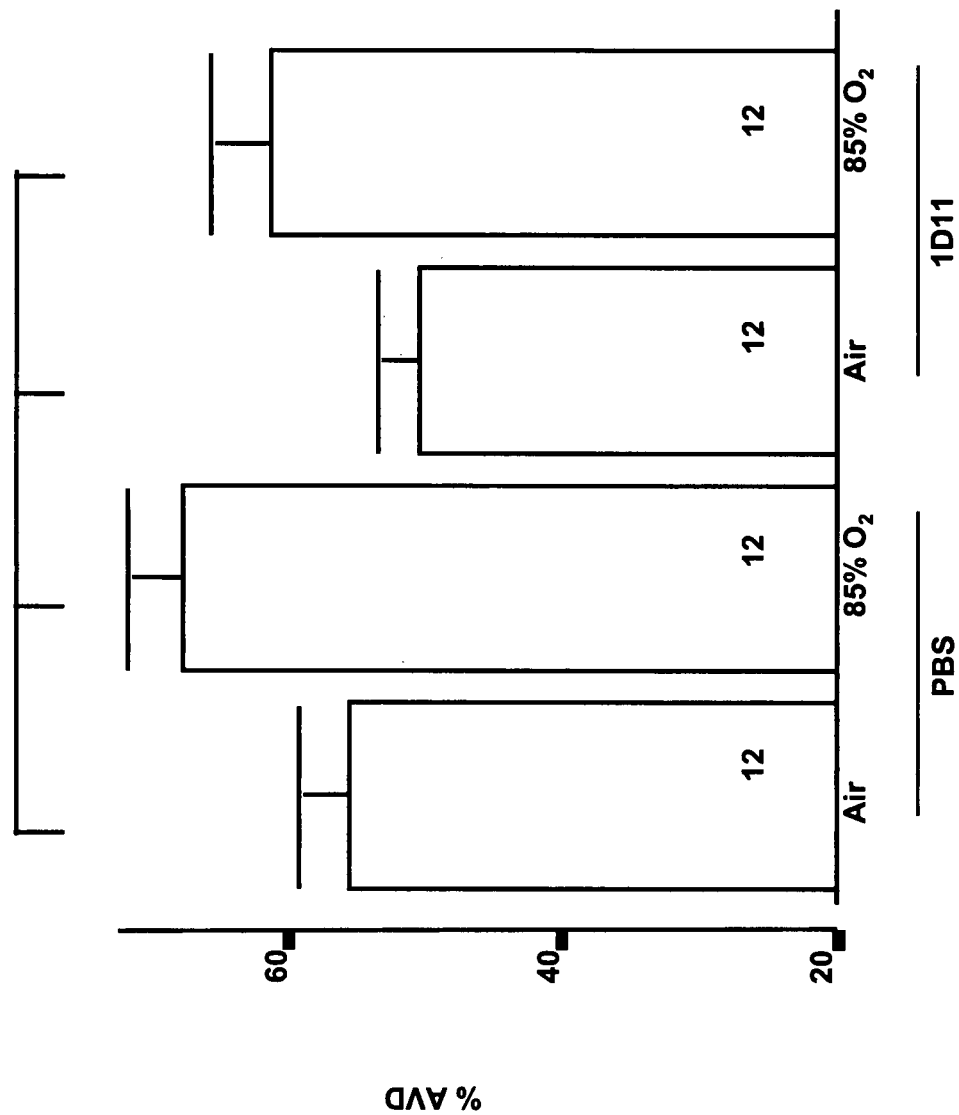
Figure 5C:
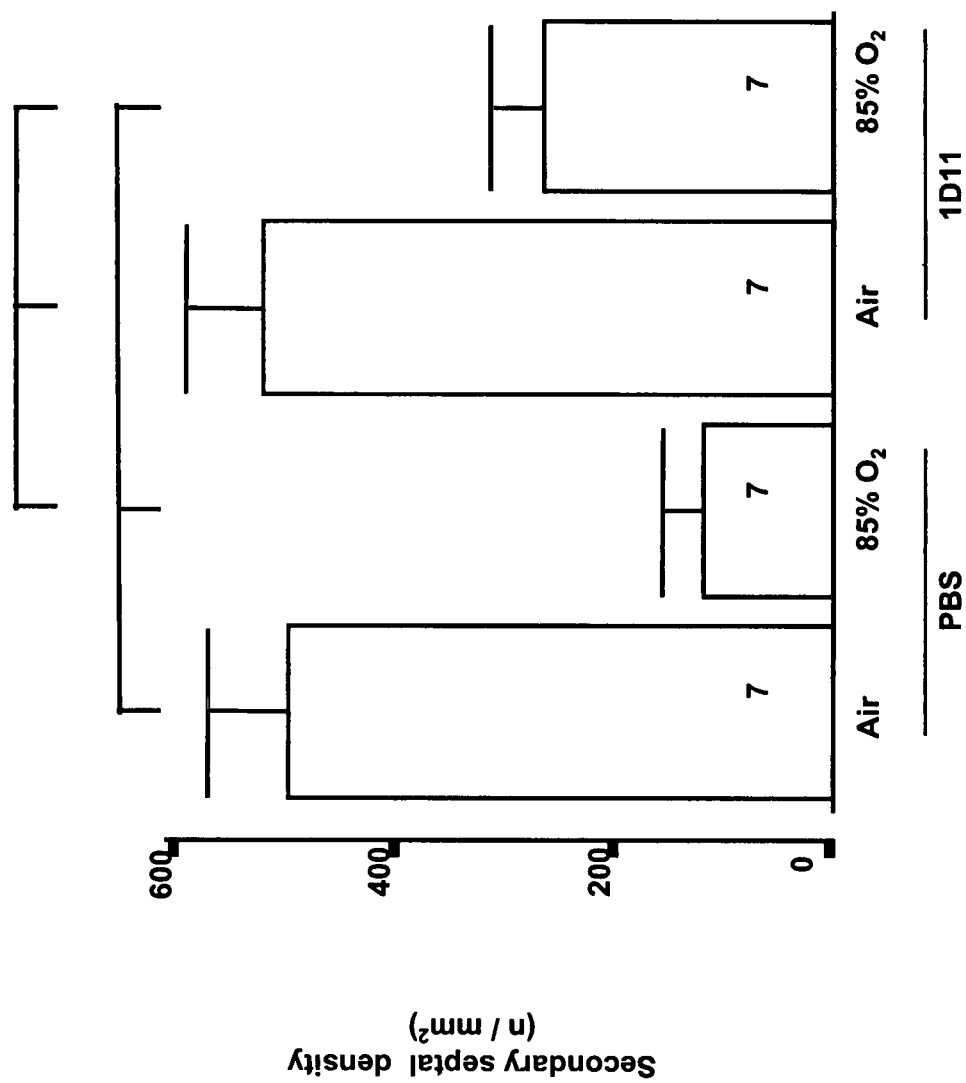

As shown in FIGS. 5A-5C, chronically breathing 85% $O_2$ was associated with a 30% increase in Lm (PBS-air 50.7±3.4 μm vs. PBS-$O_2$ 67.3±3.7 μm), ~20% increase in % AVD (PBS-air 55.6±3.7% vs. PBS-$O_2$ 67.8±4.0%) and a decrease in secondary septal density in comparison with exposure to air. Importantly, in comparison with this change associated with exposure to PBS and $O_2$, treatment of $O_2$-breathing lungs with 1D11 was associated with a 30% decrease in Lm (1D11-$O_2$ 62.3±4.4 μm), 51% decrease in % AVD (1D11-$O_2$ 61.6±4.2%), and an improvement (38% increase) in secondary septal density. These data indicate that TGF-β has an important role in mediating the effect of injury on terminal lung development. Interestingly, treatment with anti-TGF-β antibody alone was also associated with a modest decrease in Lm and % AVD. Since the basal TGF-β signaling observed in the control lungs appeared to be also modulated by 1D11 exposure, these later data indicate that TGF-β regulates the rate of postnatal alveolarization in the newborn lung.

Additional studies were performed to investigate whether the protective effect of 1D11 was due to its, isotype, $IgG_1$. Therefore, whether or not $IgG_1$ protects the hyperoxic newborn mouse lung from inhibition of alveologenesis was tested using stereological methods. Antenatal exposure to MOPC21, a 1D11 IgG isotype-matched control monoclonal antibody without a known antigen, did not attenuate the inhibition of alveologenesis induced by chronic exposure to 85% $O_2$. No difference in Lm and % AVD was observed in the lungs of animals exposed to 85% $O_2$ and treated with MOPC21 or PBS (Lm: MOPC21-$O_2$ 70.4±7.1 μm vs. PBS-$O_2$ 68.0±3.7 μm; % AVD: MOPC21-$O_2$ 69.4±2.6% vs. PBS-$O_2$ 68.9±4.5%, both P>0.05). These data agree with other reports that non-specific IgG does not protect the newborn lung from hyperoxia-induced inhibition of alveologenesis (Padela et al., *Am. J. Respir. Crit. Care Med.* 172:907-914 (2005)).

Example 3

Figure 6:
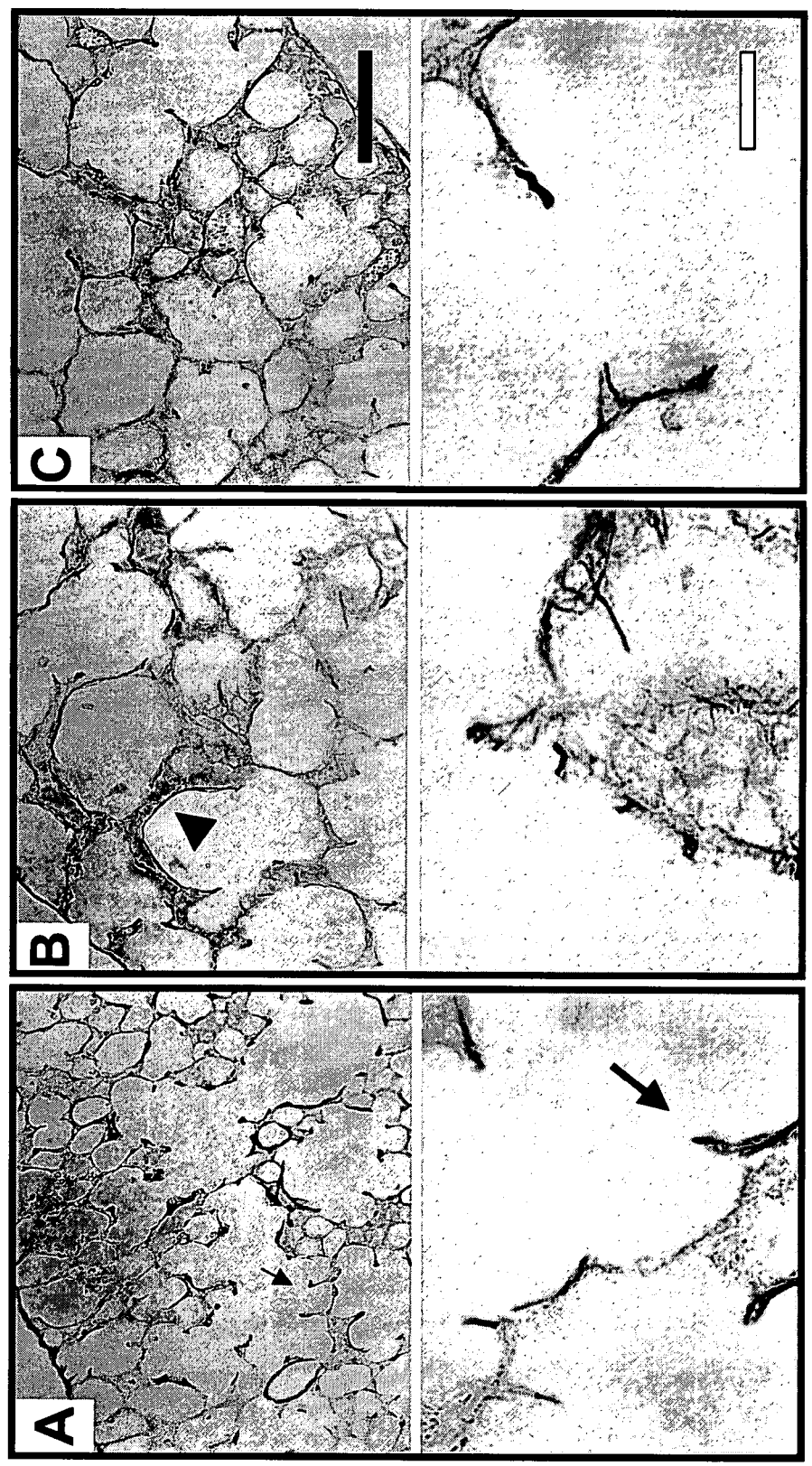
FIGS. 6A-6C are photomicrographs, which show that elastin expression was improved in the injured newborn lung treated with anti-TGF-β antibodies. Miller's elastin staining (black) of the peripheral lungs of 10 day-old mouse pups is shown for animals treated with: PBS and air (FIG. 6A), PBS and 85% $O_2$ (FIG. 6B), and 1D11 and 85% $O_2$ (FIG. 6C). Elastin was expressed in the periphery of control pup lungs where high levels were observed in the tips of secondary septa (arrows). Chronic exposure to a high level of $O_2$ was associated with a decrease in the localization of elastin in the septae and an increase of its association with the saccule wall (arrow head.
Figure 7A:
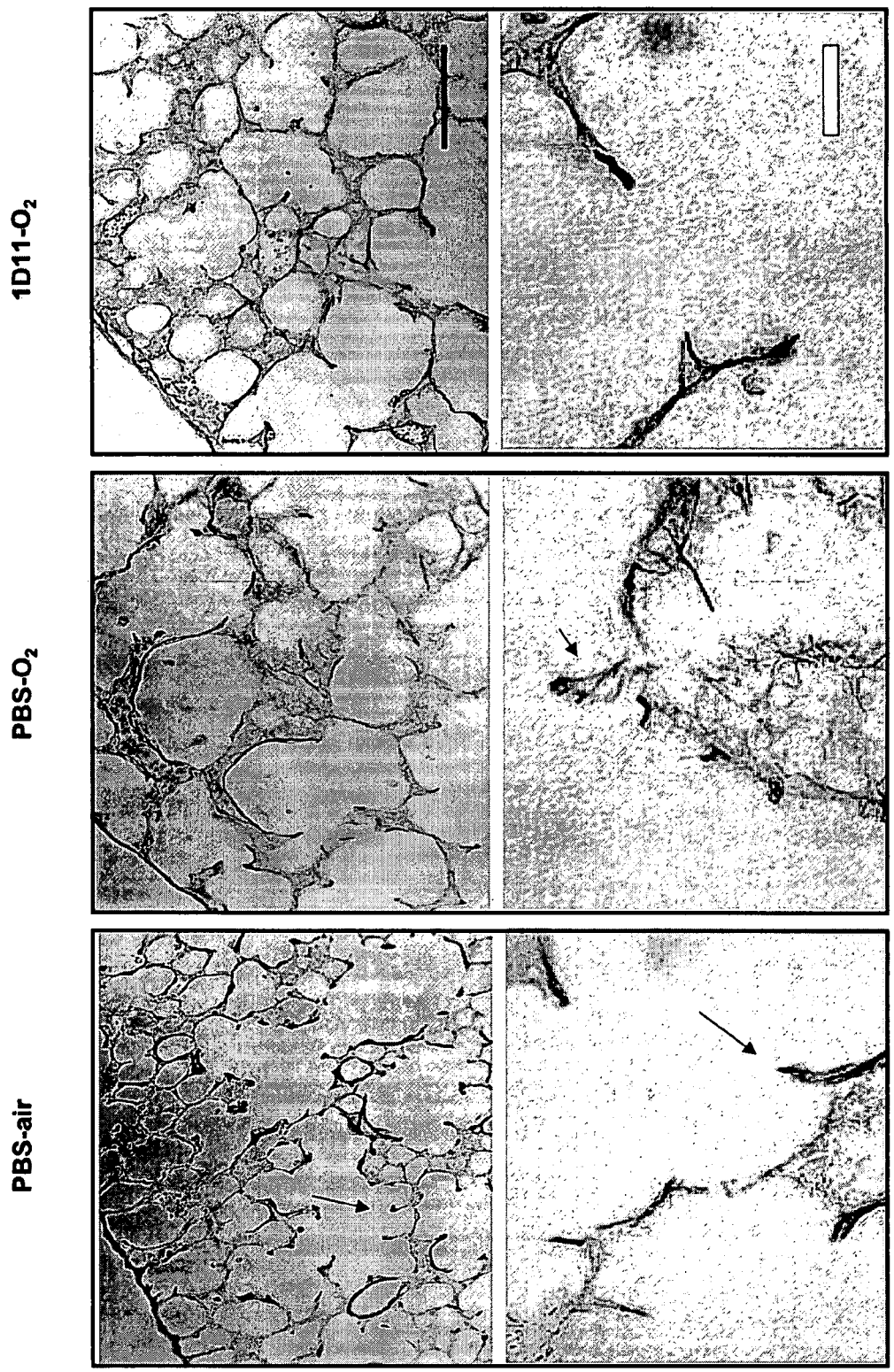

Alveolar Septal Elastin Organization is Improved by Anti-TGF-β Treatment in the Injured Newborn Lung Elastin is an important component of the alveolar wall and lung vasculature, and its biosynthesis and extracellular assembly is critical for normal lung development. In the lungs of infants with BPD, as in newborn mice with lung injury (Veness-Meehan et al., *Pediatr. Res.* 48:434-444 (2002)), the normal organization of elastin in the tips of the secondary crests is disrupted, and elastin is instead observed in the walls of the distal airways. Because TGF-β regulates the expression and degradation of, ECM proteins in mesenchymal cells (Leask et al., *Faseb J.* 18:816-827 (2004)) and in the lung (Kucich et al., *Am. J. Respir. Cell Mol. Biol.* 17:10-16 (1997); Parks et al., *Am. J. Respir. Cell Mol. Biol.* 17:1-2 (1997)), the effect of treatment with 1D11 on extracellular matrix protein deposition was examined. As shown in FIG. 6, chronically breathing high levels of $O_2$ was associated with altered elastin expression in the secondary septae. The typical pattern of elastin expression observed in PBS treated, air-breathing pups (arrows) was more disordered and spread throughout the septal wall (arrow head). As shown in FIGS. 7A and 7B, the disordered elastin expression pattern was associated with an increase in the % EVD. Importantly, treatment with 1D11 was associated with an improved elastin deposition pattern in the secondary crests of oxygen-treated lungs and a % EVD that was normal. These data indicate that TGF-β has an important role in mediating the abnormal expression of elastin in hyperoxic lung injury. Furthermore, they also indicate that treatment with an anti-TGF-β antibody can protect the injured newborn lung from disordered elastin formation. At this early stage in lung injury, no change in the distribution of collagen was observed in the mouse pup lungs exposed to oxygen (data not shown).

Example 4

Figure 8:
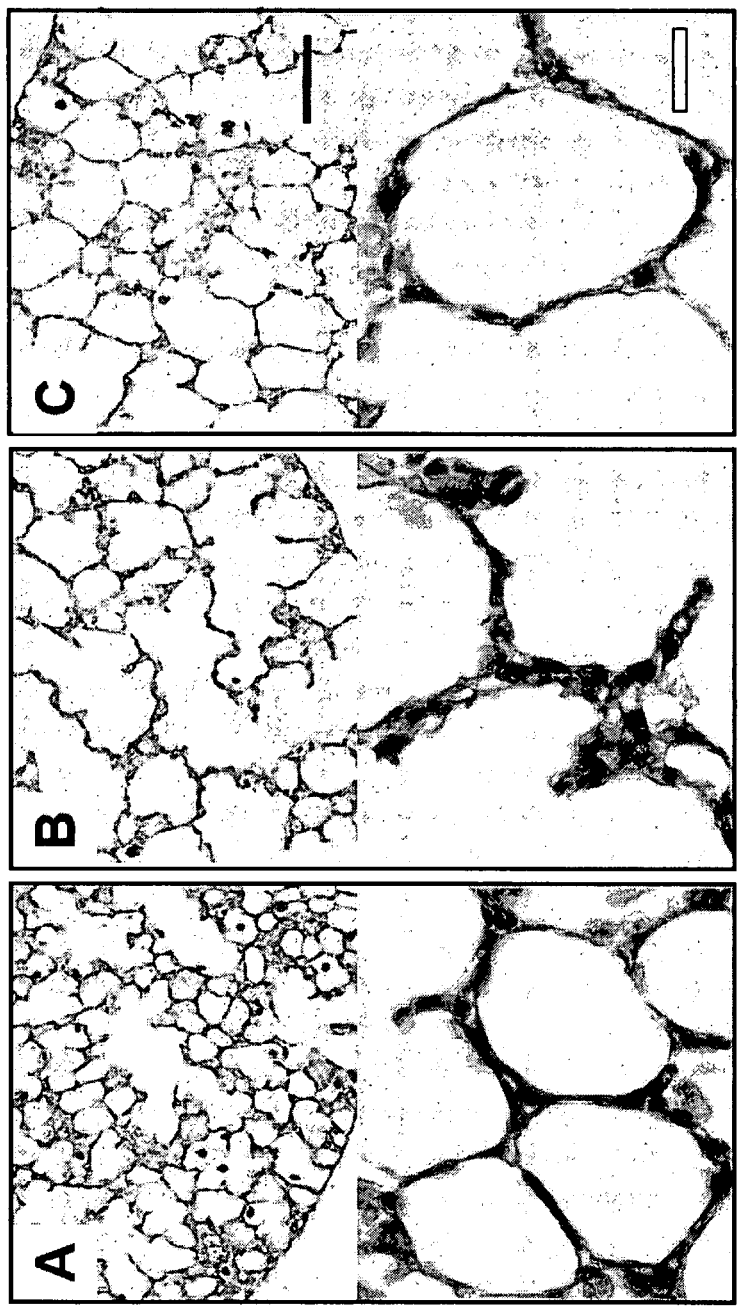
FIGS. 8A-8C are photomicrographs, which show that a marked improvement in pulmonary microvascular endothelial cell pattern occurs in injured lungs treated with anti-TGF-β antibodies. *Griffonia simplicifolia* lectin staining of endothelial cell α-D-galactosides in the peripheral lungs of 10 day-old mouse pup lungs is shown for animals treated with: PBS and air (FIG. 8A), PBS and 85% $O_2$ (FIG. 8B), and 1D11 and 85% $O_2$ (FIG. 8C). Septal walls of pup lungs exposed to 85% $O_2$ were thickened and had an anfractuous pattern of endothelial cell staining. In contrast, the lungs treated with 1D11 and high levels of oxygen had a more organized endothelial cell pattern. All panels were counterstained with hematoxylin. Closed scale bar: 100 μm; open scale bar: 20 μm.
Figure 9:
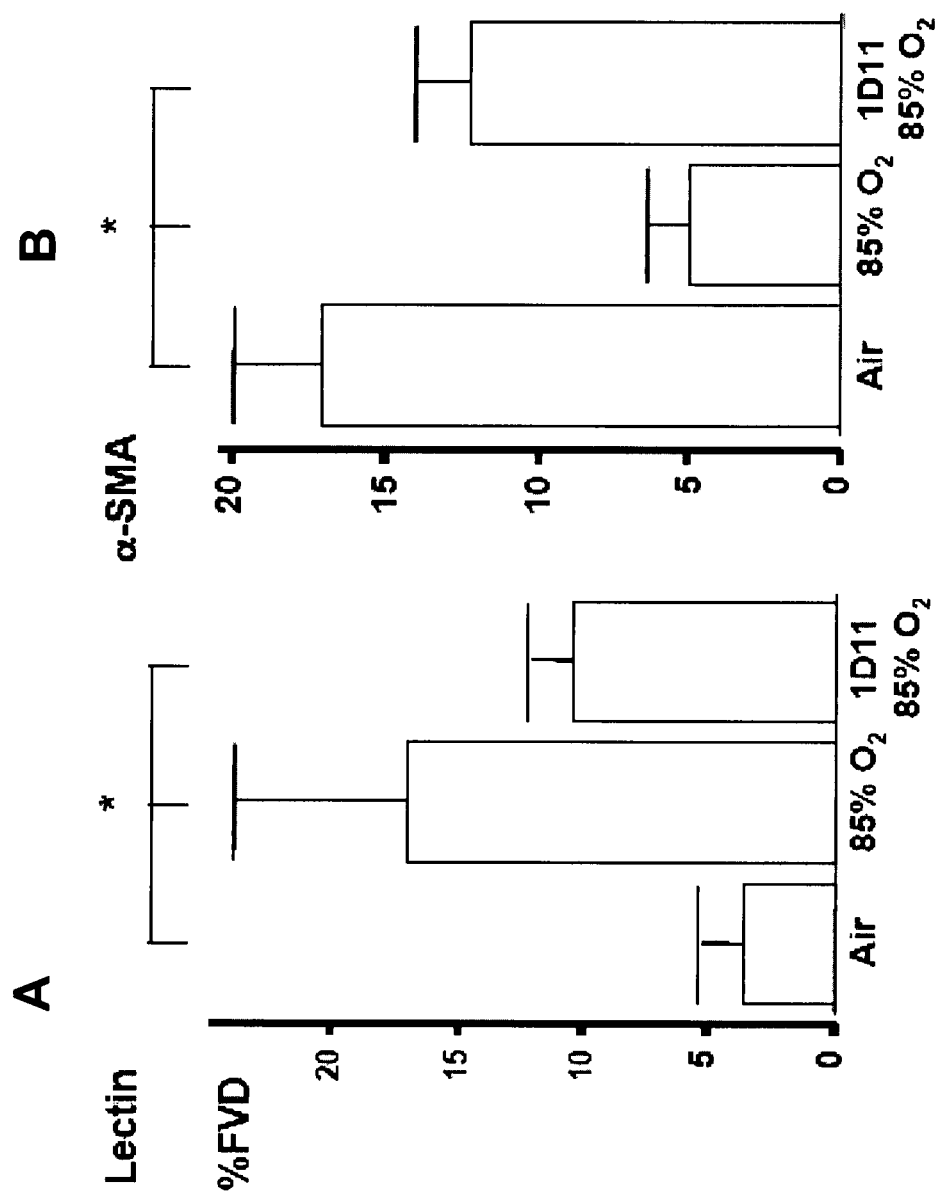
FIGS. 9A-9B are graphical representations of experiments, which show that treatment with anti-TGF-β antibody improved objective, quantitative indices of pulmonary microvascular development in the injured lung. The % fluorescent volume density (% FVD) (FIG. 9A) of endothelial cells and SMC (FIG. 9B) in the peripheral lung was examined using pup lungs reacted with lectin and an αSMA antibody, respectively. Injury of the developing lung was associated with an increase in lectin and decrease in αSMA % FVD. In contrast, exposure to TGF-β-neutralizing antibodies improved the volume density of these pulmonary microvascular cells markers. N=7 each group; *, P<0.05.

Treatment with an Anti-TGF-β Antibody Improves Pulmonary Microvascular Development in the Hyperoxic Developing Lung In the developing mouse and rat, exposure to high levels of oxygen alters normal pulmonary microvascular development (Roberts et al., *Pediatr. Res.* 17:368-375 (1983)); D'Angio et al., *Front. Biosci.* 7:d1609-1623 (2002)). TGF-β has been reported to play a role in regulating the differentiation of cells that form blood vessels (Roberts et al., *Am. Rev. Respir. Dis.* 140:1126-1128 (1989)). Therefore, a study was conducted to determine whether an anti-TGF-β antibody can improve the abnormal pulmonary microvascular development observed in the $O_2$-injured newborn pup lung. As shown in FIG. 8, chronic exposure to 85% $O_2$ was associated with dysmorphic pulmonary microvascular assembly. The staining pattern of pulmonary microvascular endothelial cells with lectin was more diffuse and less orderly than that observed in the control lung exposed to air. This was also associated with an increase in the volume density of lectin-stained cells in the periphery of the injured pup lungs; the % FVD for lectin was increased by approximately 4-fold in the pup lungs exposed to 85% $O_2$ for 10 days (FIG. 9). Furthermore, treatment with 1D11 was associated with a similar pattern of endothelial cell arrangement in the distal airways of lungs treated with 85% $O_2$. In addition, exposure to 1D11 was associated with nearly a 50% reduction in lectin % FVD in lungs exposed to a high level of $O_2$. These data indicate that TGF-β disrupts normal pulmonary microvascular development in the injured newborn lung and that neutralization of the TGF-β with antibodies can attenuate abnormal pulmonary vascular development.

Figure 10:
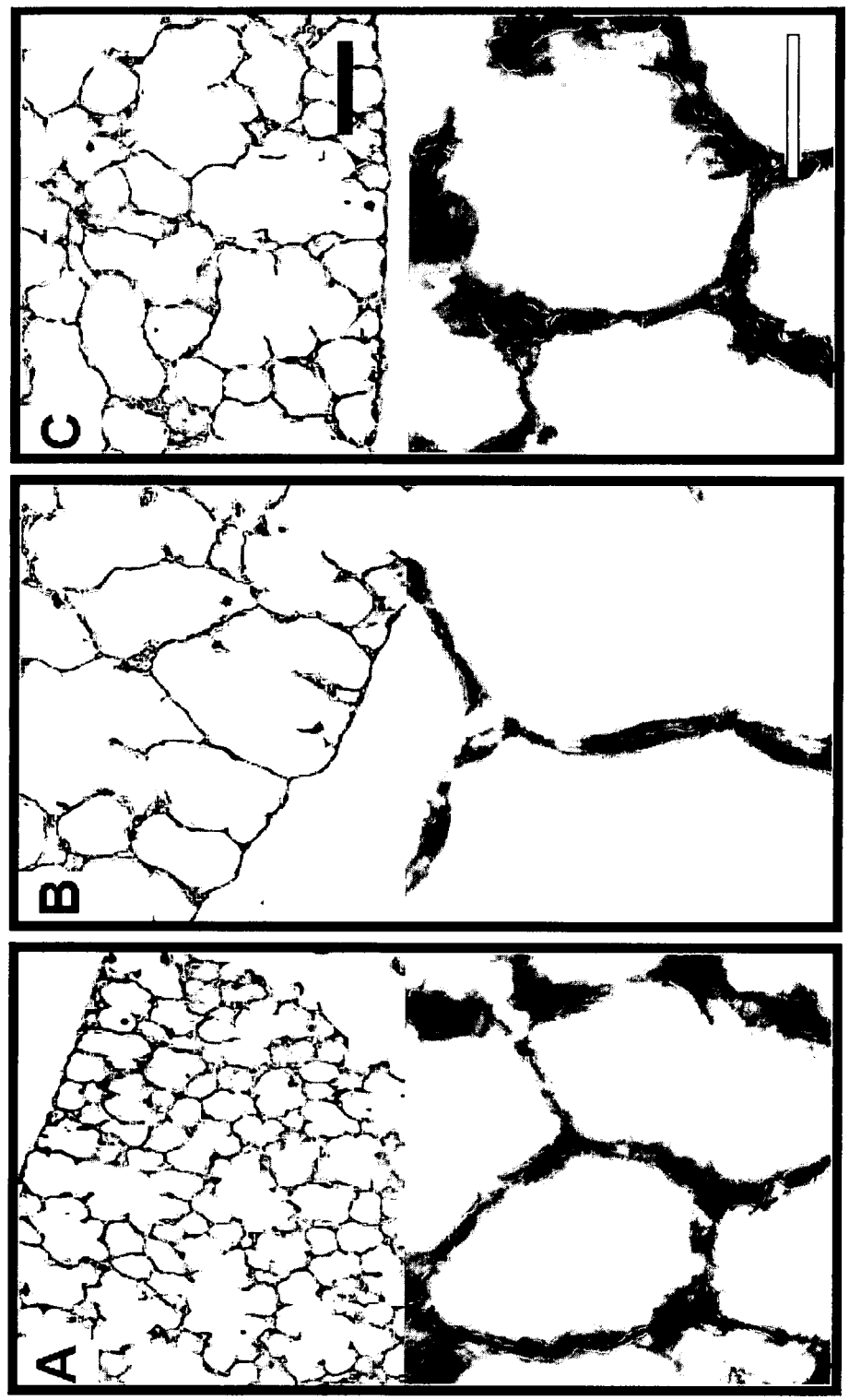
FIGS. 10A-10C show normalization of the pulmonary microvascular myofibroblast cells in the injured newborn lung treated with anti-TGF-β antibodies. αSMA immunoreactivity (dark staining) is shown in cells of the peripheral lungs of 10 day-old mouse pup lungs treated with: PBS and air (FIG. 10A), PBS and 85% $O_2$ (FIG. 10B), and 1D11 and 85% $O_2$ (FIG. 10C). In comparison with lungs of mouse, pups who breathed air, those exposed to high levels of $O_2$ have less αSMA immunoreactivity in the lung periphery. The lungs of pups treated with 1D11 and high levels of oxygen appeared to have more αSMA immunoreactivity in the walls of distal airways. All panels were counterstained with toluidine blue. Closed scale bar: 100 µm; open scale bar: 20 µm.

Since smooth muscle cells (SMC) influence pulmonary microvascular development, an examination was made to determine whether attenuation of abnormal TGF-β signaling in the injured newborn lung with TGF-β neutralizing antibody was associated with an improved distribution of myofibroblasts. As shown in FIG. 10, hyperoxic pulmonary injury was associated with a decrease in αSMA-identified myofibroblasts in the walls of the distal lung. The % FVD of αSMA was decreased by nearly 70% in the pup lungs chronically exposed to 85% $O_2$ (FIG. 9). In contrast, treatment with anti-TGF-β antibodies increased the amount of αSMA immunoreactivity and the % FVD in the injured lung. These data indicate that TGF-β neutralization had a salutary effect on the injured pulmonary microvasculature of the newborn. In this model, immunohistochemistry with αSMA antibodies did not reveal an increase in pulmonary artery muscularization in pup lungs exposed to 85% $O_2$ for 10 days (data not shown). In addition, the right ventricular mass of the pups chronically breathing high levels of oxygen was not increased (RV:LV+S: PBS-air 0.32±0.04; PBS-85% $O_2$ 0.25±0.05, P>0.05).

Example 5

Somatic Growth and Treatment with Anti-TGF-β Antibodies

Hyperoxic lung injury in the newborn is associated with decreased somatic growth. Because treatment with anti-TGF-β antibody was associated with improved peripheral lung alveologenesis and vasculogenesis, a study was conducted to determine whether treatment with 1D11 has a salutary effect on the growth of pups exposed to 85% $O_2$. Exposure of newborn mouse pups to high levels of oxygen was associated with an almost 30% decrease in weight in comparison to control pups breathing air (body weight at 10 days of age: PBS-air: 5.26±1.18 gm, PBS-85% $O_2$: 3.74±1.0 gm; n=10-15, P<0.05). The weight of pups treated with 1D11 and exposed to 85% $O_2$ (4.62±0.85 gm) was not significantly different from the weight of air-breathing controls.

In the foregoing examples, exposure to a pan-specific anti-TGF-β antibody promoted lung development in mouse pups with pulmonary injury. Continuous inhalation of high levels of $O_2$ was observed to decrease alveologenesis and alter vasculogenesis during the critical terminal stage of lung development, as previously reported (Roberts et al., *Pediatr. Res.* 17:368-375 (1983); Warner et al., *Am. J. Physiol.* 275:L110-117 (1998); D'Angio et al., *Front. Biosci.* 7:d1609-1623 (2002)). This produced pathological findings in the hyperoxic mouse pup that are similar to those observed in newborn human beings with BPD. Importantly, exposure to an anti-TGF-β antibody, commencing in the antenatal period, improved the alveolar development, elastin deposition, and microvascular structure in the injured newborn pup lungs.

The results of these studies demonstrate for the first time that anti-TGF-β therapies can protect the injured newborn lung from inhibition of alveologenesis and vasculogenesis and serve as a treatment for BPD.

The specification is most thoroughly understood in light of the teachings of the references cited within the specification. The embodiments within the specification provide an illustration of embodiments of the invention and should not be construed to limit the scope of the invention. The skilled artisan readily recognizes that many other embodiments are encompassed by the invention. All publications, patents, patent applications, and biological sequences cited in this disclosure are incorporated by reference in their entirety. The citation of any references herein is not an admission that such references are prior art to the present invention.

Unless otherwise indicated, all numbers expressing quantities of ingredients, cell culture, treatment conditions, and so forth, used in the specification, including claims, are to be understood as being optionally modified in all instances by the term "about." Accordingly, unless otherwise indicated to the contrary, the numerical parameters are approximations and may vary depending upon the desired properties sought to be obtained by the present invention. Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the following claims.

We claim:

1. A method of treating a subject chosen from an infant or fetus at risk of developing bronchopulmonary dysplasia comprising administering a therapeutically effective amount of a TGF-β antagonist to the subject and at least one additional agent or therapy, which is chosen from a surfactant, oxygen therapy, ventilator therapy, a steroid, vitamin A, inhaled nitric oxide, high calorie nutritional formulation, a diuretic, and a bronchodilator if the subject is an infant, or is chosen from a steroid, vitamin A, and a diuretic if the subject is a fetus.

2. The method of claim 1, wherein the subject is a fetus and the TGF-β antagonist is administered to the fetus during the prenatal period.

3. The method of claim 2, wherein the TGF-β antagonist is administered to the fetus by administration to the mother prior to birth of the fetus.

4. The method of claim 2, wherein the TGF-β antagonist is administered directly to the fetus in utero.

5. The method of claim 1, wherein the subject is an infant and the TGF-β antagonist is administered to the infant during the postnatal period.

6. The method of claim 1, wherein the age of the subject is about 24 weeks gestation to about 6 months after birth.

7. The method of claim 1, wherein the subject is a premature infant born at an age of about 24 to about 32 weeks gestation.

8. The method of claim 1, wherein the subject is an infant and the weight of the infant at birth is about 1500 grams or less.

9. The method of claim 1, wherein the subject is an infant and the weight of the infant at birth is about 1000 grams or less.

10. The method of claim 1, wherein the TGF-β antagonist is selected from the group consisting of an anti-TGF-β antibody, an anti-TGF-β receptor antibody, and a soluble TGF-β receptor.

11. The method of claim 10, wherein the antibody is a humanized form of monoclonal antibody 1D11, wherein monoclonal antibody 1D11 is the antibody obtainable from the hybridoma deposited at the American Type Culture Collection under Designation No. HB 9849.

12. The method of claim 1, wherein the TGF-β antagonist is a monoclonal antibody administered at a dose having a potency equivalent to the potency of the 1D11 antibody at a dose of 0.1 to 10 mg/kg body weight.

13. The method of claim 1, wherein the TGF-β antagonist is a monoclonal antibody administered at a dose having a potency equivalent to the potency of the 1D11 antibody at a dose of 1 mg/kg body weight.

14. The method of claim 1, wherein the TGF-β antagonist is a pan-specific human or humanized monoclonal antibody.

15. The method of claim 1, wherein the TGF-β antagonist is administered intramuscularly, intravenously, or subcutaneously.

16. The method of claim 1, wherein the TGF-β antagonist is inhaled in an aerosolized form.

17. The method of claim 16, where the TGF-β antagonist is administered by a nebulizer or an inhaler.

18. The method of claim 16, wherein said aerosolized form comprises droplets less than 10 μm in diameter, said droplets comprising the TGF-β antagonist in a suitable pharmacologically acceptable liquid carrier.

19. The method of claim 1, wherein the TGF-β antagonist is inhaled in powder form comprising particles less than 10 μm in diameter.

20. The method of claim 1, wherein the subject is an infant and the at least one additional agent or therapy is selected from the group consisting of oxygen therapy, ventilator therapy, inhaled nitric oxide, and a bronchodilator.

21. A method of treating bronchopulmonary dysplasia comprising administering a therapeutically effective amount of a TGF-β antagonist perinatally or postnatally and at least one additional agent or therapy, which is chosen from a surfactant, oxygen therapy, ventilator therapy, a steroid, vitamin A, inhaled nitric oxide, high calorie nutritional formulation, a diuretic, and a bronchodilator, to an infant in need thereof.

22. The method of claim 21, wherein the TGF-β antagonist is used to ameliorate bronchopulmonary dysplasia in an infant that has been diagnosed with the disease.

23. A method of treating hyperoxic lung injury in an infant, comprising:
    administering a therapeutically effective amount of a TGF-β antagonist to the infant perinatally or postnatally; and
    providing oxygen supplementation to the infant after birth.

24. The method of claim 23, wherein the TGF-β antagonist is selected from the group consisting of an anti-TGF-β antibody, an anti-TGF-β receptor antibody, and a soluble TGF-β receptor.

* * * * *

UNITED STATES PATENT AND TRADEMARK OFFICE
CERTIFICATE OF CORRECTION

PATENT NO. : 8,642,034 B2
APPLICATION NO. : 12/444059
DATED : February 4, 2014
INVENTOR(S) : James B. Streisand et al.

Page 1 of 1

It is certified that error appears in the above-identified patent and that said Letters Patent is hereby corrected as shown below:

On the Title Page, Item (73), in the "Assignee":
"(73) Assignee: Genzyme Corporation, Cambridge, MA (US)"
should read
--(73) Assignees: Genzyme Corporation, Cambridge, MA (US);
The General Hospital Corporation, Boston, MA (US)--.

Signed and Sealed this
Eighteenth Day of November, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,642,034 B2
APPLICATION NO. : 12/444059
DATED : February 4, 2014
INVENTOR(S) : Streisand et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 719 days.

Signed and Sealed this
Fifth Day of January, 2016

Michelle K. Lee
*Director of the United States Patent and Trademark Office*